(12) United States Patent
Lee et al.

(10) Patent No.: US 10,379,089 B2
(45) Date of Patent: Aug. 13, 2019

(54) THERMAL GRADIENT CHROMATOGRAPHY DEVICES AND METHODS OF USING THEM

(71) Applicants: Edgar D Lee, Wallsburg, UT (US); Nathan L Porter, Kaysville, UT (US); Randal W Waite, Springville, UT (US)

(72) Inventors: Edgar D Lee, Wallsburg, UT (US); Nathan L Porter, Kaysville, UT (US); Randal W Waite, Springville, UT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 164 days.

(21) Appl. No.: 15/338,360

(22) Filed: Oct. 29, 2016

(65) Prior Publication Data

US 2017/0131243 A1 May 11, 2017

Related U.S. Application Data

(60) Provisional application No. 62/248,918, filed on Oct. 30, 2015.

(51) Int. Cl.
*G01N 30/30* (2006.01)

(52) U.S. Cl.
CPC ..... *G01N 30/30* (2013.01); *G01N 2030/3015* (2013.01)

(58) Field of Classification Search
CPC .................. G01N 30/30; G01N 2030/3015
USPC ...................................................... 73/61.52
See application file for complete search history.

(56) References Cited

U.S. PATENT DOCUMENTS

| | | | | |
|---|---|---|---|---|
| 3,146,616 A * | 9/1964 | Loyd | ................... | G01N 30/30 219/772 |
| 3,363,447 A * | 1/1968 | Severs | ................... | G01N 30/30 219/388 |
| 3,622,276 A * | 11/1971 | Haahti | ................... | G01N 30/50 422/89 |
| 4,599,169 A * | 7/1986 | Ray | ................... | G01N 30/30 210/175 |
| 5,028,243 A * | 7/1991 | Rubey | ................... | G01N 30/30 95/87 |
| 5,215,556 A | 6/1993 | Hiller | | |
| 5,807,426 A | 9/1998 | Ohtsuki | | |
| 6,007,602 A * | 12/1999 | Ledford, Jr. | ......... | G01N 30/463 210/198.2 |
| 2008/0135484 A1 | 6/2008 | Hammer | | |
| 2010/0005867 A1 | 1/2010 | Doerr | | |

(Continued)

OTHER PUBLICATIONS

ISR/WO for PCT/US16/59608 dated Apr. 12, 2016.

*Primary Examiner* — Marrit Eyassu
(74) *Attorney, Agent, or Firm* — Rhodes IP PLC; Christopher R Rhodes

(57) ABSTRACT

Certain configurations described herein are directed to gas chromatography devices. In some instances, the gas chromatography devices may comprise at least one heating device which can be moved along a chromatography column to provide a thermal gradient to the chromatography column. In other instances, the gas chromatography devices may comprise a heating device that can receive a moving chromatography column to provide a thermal gradient to the chromatography column. The gas chromatography devices may be configured as portable devices which can be used to perform remote analyzes.

20 Claims, 18 Drawing Sheets

(56) References Cited

U.S. PATENT DOCUMENTS

2012/0318172 A1    12/2012  Collins
2013/0277350 A1*   10/2013  Arima .................... G01N 30/30
                                                        219/201
2015/0192549 A1*    7/2015  Takahashi .............. G01N 30/30
                                                        73/61.55
2016/0132617 A1*    5/2016  Liu ..................... G06F 17/5009
                                                        703/2

* cited by examiner

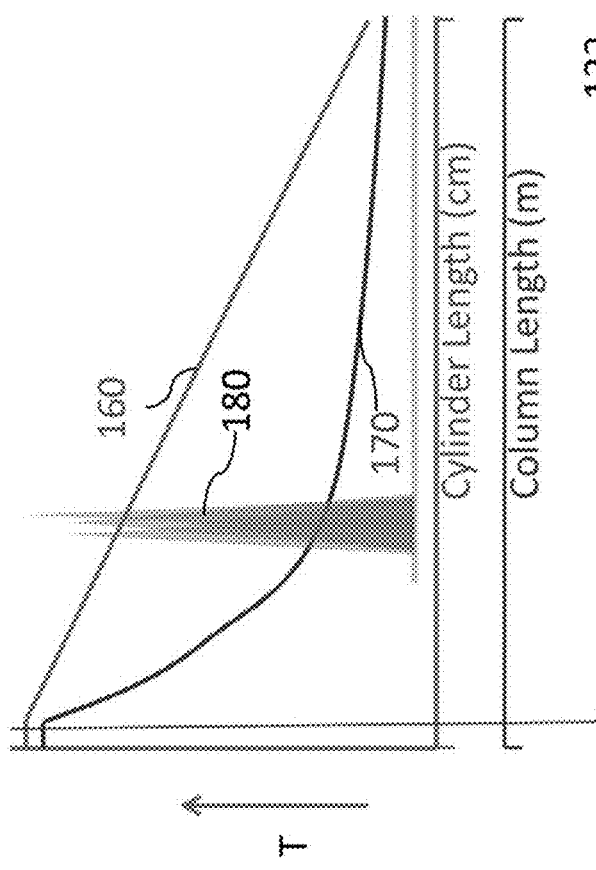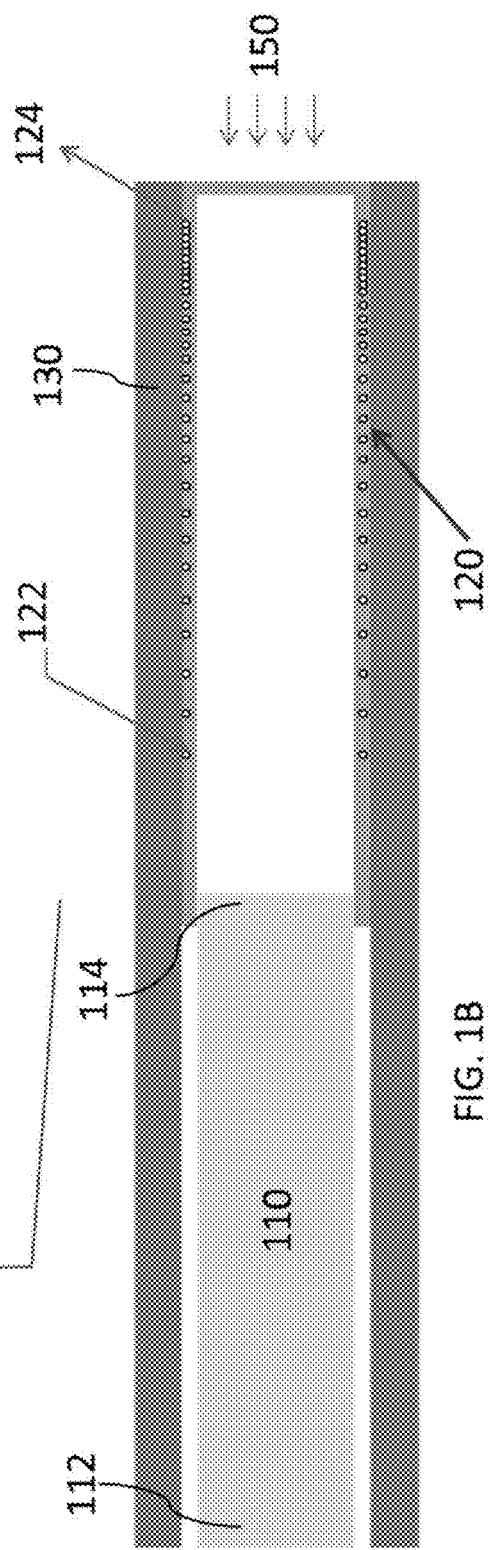

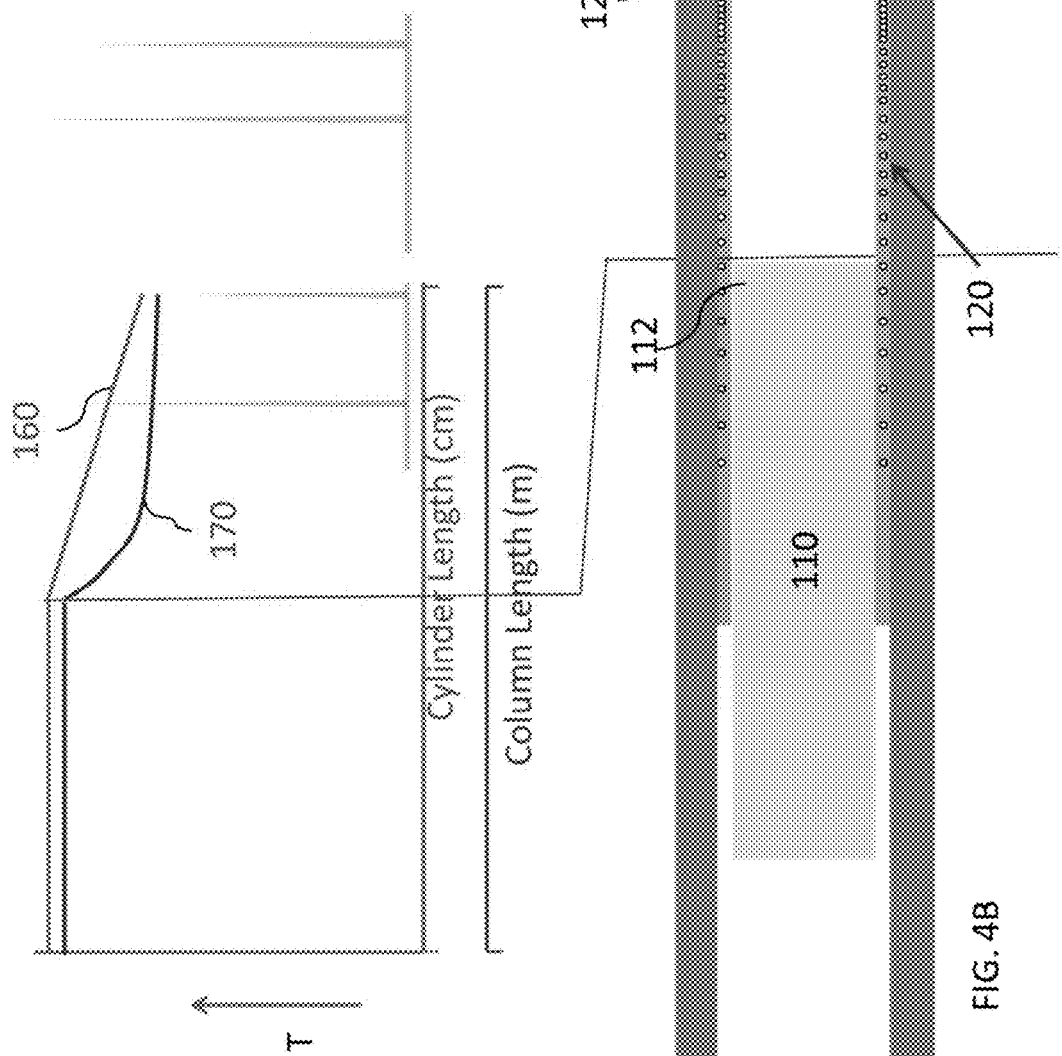

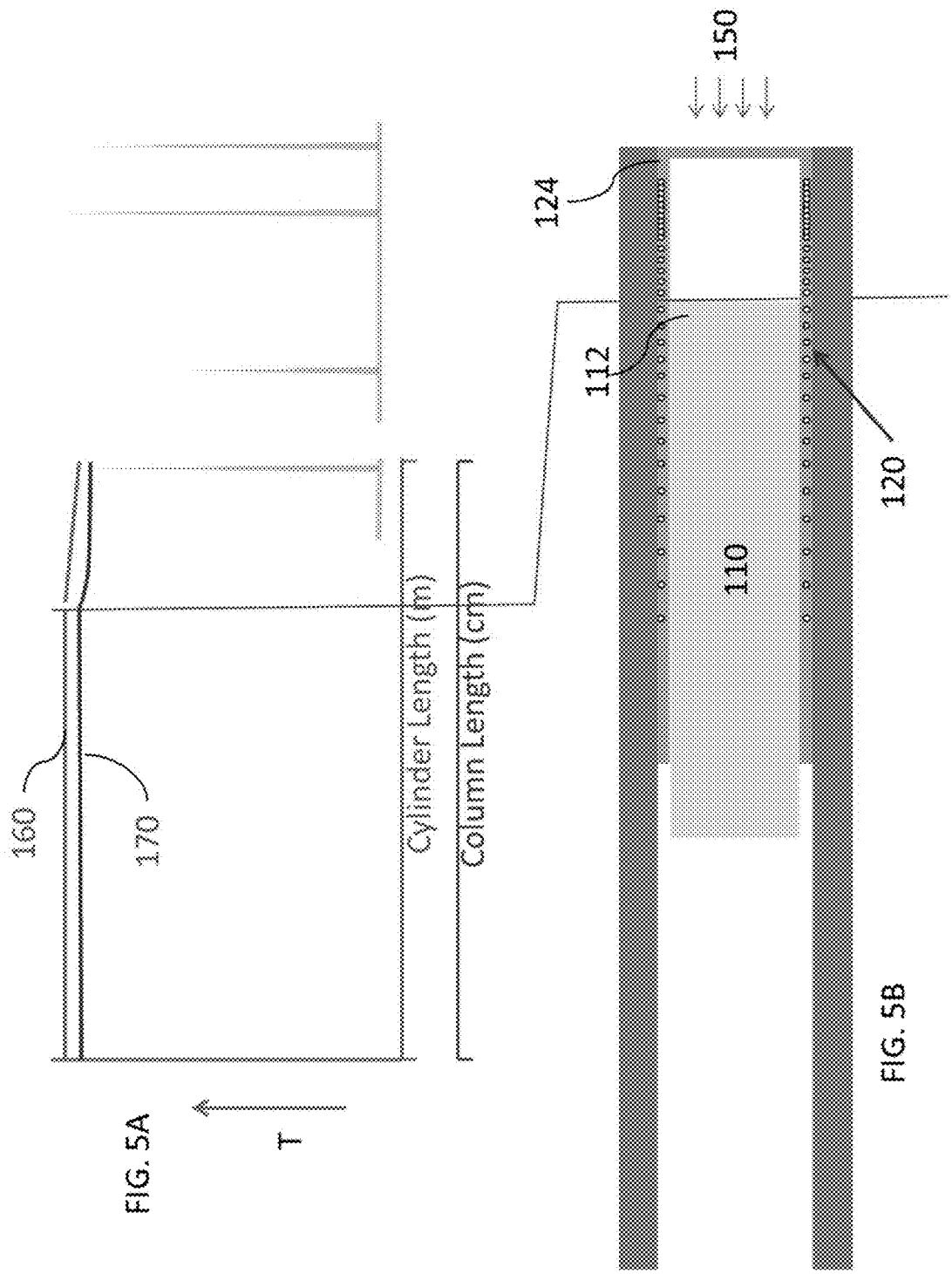

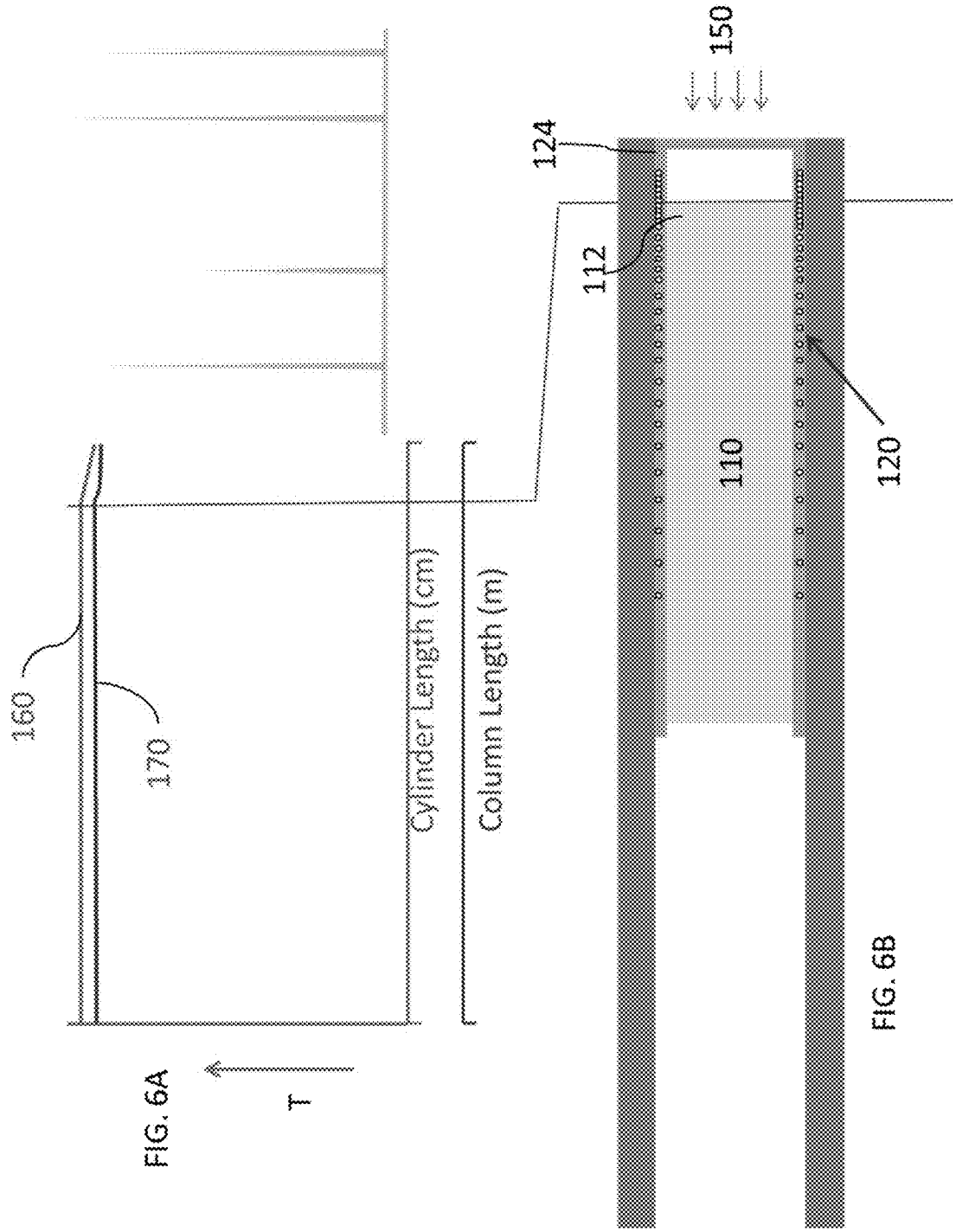

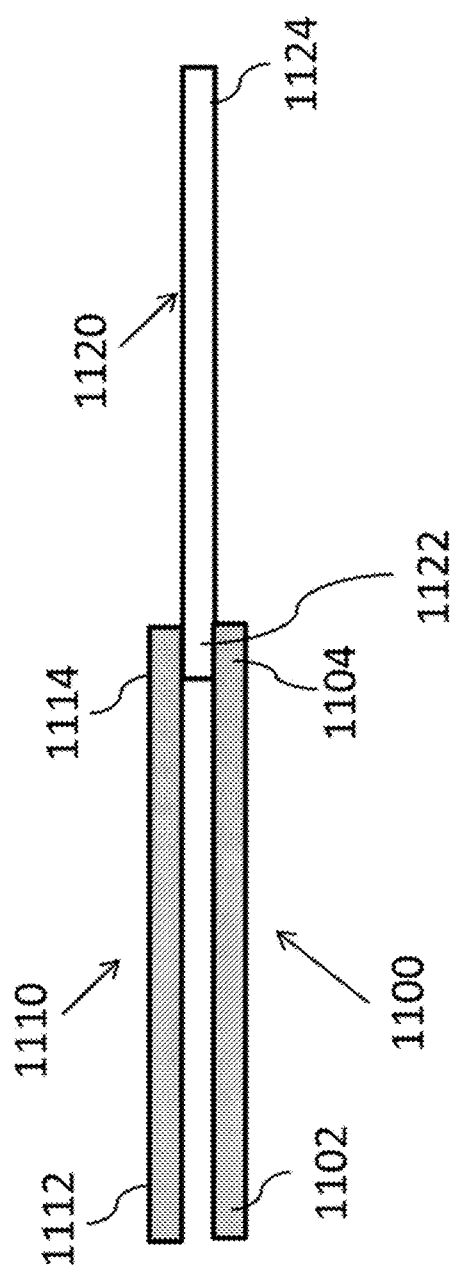
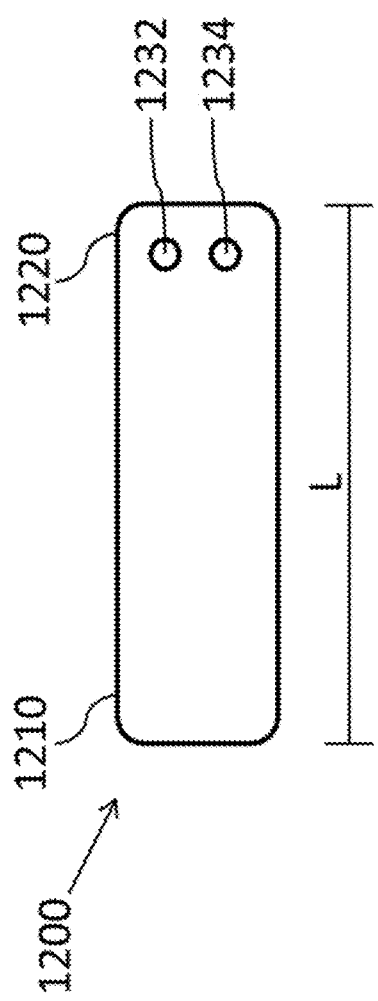

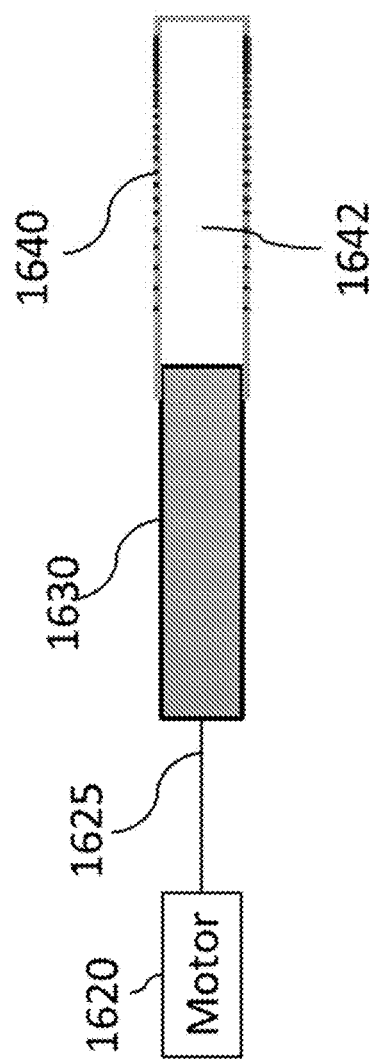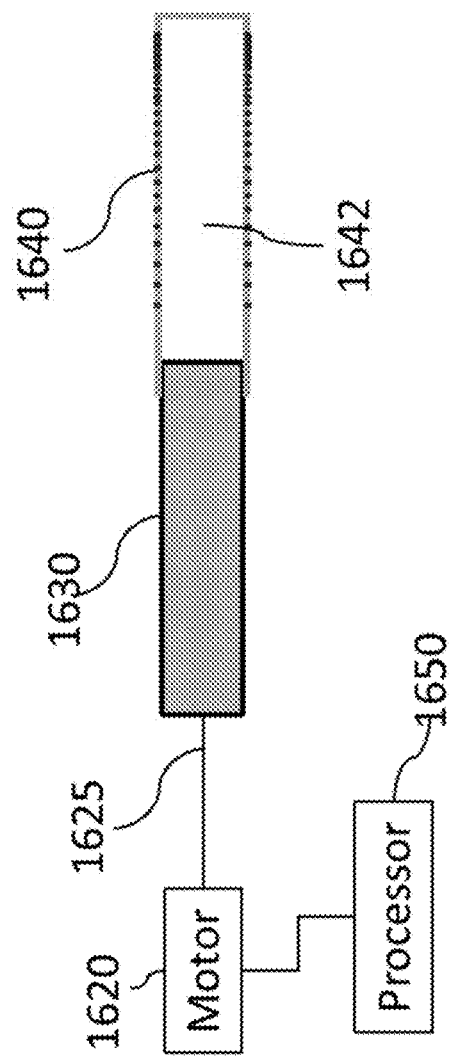

THERMAL GRADIENT CHROMATOGRAPHY DEVICES AND METHODS OF USING THEM

PRIORITY APPLICATION

This application is related to and claims priority to and the benefit of U.S. Provisional Application No. 62/248,918 filed on Oct. 30, 2015, the entire disclosure of which is hereby incorporated herein by reference for all purposes.

TECHNOLOGICAL FIELD

Certain embodiments described herein are related to chromatography devices. More particularly, certain configurations are disclosed that are directed to heating devices which can provide a thermal gradient to a chromatography column during a chromatographic separation.

BACKGROUND

Chromatography devices can be used to separate two or more components present in a mixture. The components are typically introduced into a chromatography system to separate the components based on their differential solubilities between a mobile phase and a stationary phase.

SUMMARY

Certain aspects described herein are directed to chromatography systems where one or both of a heating device (or multiple heating devices) and a chromatography column can be moved to provide a thermal gradient to the chromatography column during a chromatographic analysis.

In one aspect, a chromatography system comprises a heating device configured to thermally couple to an inlet section of a chromatography column in a first position and to thermally couple to an exit section of a chromatography column in a second position, the heating device configured to move from the first position to the second position during a chromatographic separation, and a processor configured to control movement of the heating device from the first position to the second position during the chromatographic separation using the heating device to provide a thermal gradient to the chromatography column during the chromatographic separation.

In certain configurations, the system comprises a motor coupled to the heating device and electrically coupled to the processor, the motor configured to move the heating device from the first position to the second position. In some configurations, the system comprises a DC power source electrically coupled to the processor. In other examples, the DC power source comprises at least one of an electrochemical cell, a fuel cell, a solar cell or a wind turbine configured to provide a direct current. In certain instances, the system comprises a display electrically coupled to the processor. In other examples, the motor is configured as a stepper motor. In certain instances, the system comprises a transmitter electrically coupled to the processor. In some embodiments, the transmitter is configured to wirelessly couple to a mobile device. In some instances, the transmitter comprises at least one of a Bluetooth device, a near field communication device, a WLAN device, a USB device, a RF device, a cellular device, a radio device, a satellite device, or a GPS device. In certain instances, the system comprises an oven configured to thermally couple to the chromatography column and to receive the heating device and the chromatography column. In certain examples, the oven is configured to operate at a substantially constant temperature during the chromatographic separation. In some embodiments, the heating device is the only heating device present in the chromatography system to provide heat to the chromatography column. In other examples, the system comprises a cooling device thermally coupled to the heating device and the chromatography column, the cooling device configured to assist in providing the thermal gradient to the chromatography column. In some examples, the cooling device is configured as one or more of a fan, a Peltier cooler, a cooling rod and a heatsink. In some examples, the heating device and the cooling device together are configured to provide a linear thermal gradient along a longitudinal dimension of the chromatography column from the inlet section to the exit section. In certain embodiments, the system comprises a detector configured to fluidically couple to the chromatography column. In certain examples, the heating device is configured as a cylinder configured to move through an interior space formed by coiling of the chromatography column. In other examples, the diameter of the cylinder is sized and arranged to receive and contact surfaces of chromatography column to provide the thermal gradient to the chromatography column. In certain embodiments, the heating device is configured to thermally couple to two or more chromatography columns during the chromatographic separation to provide a temperature gradient to each of the two or more chromatography columns. In other configurations, the system comprises a second heating device configured to thermally couple to the inlet section of the chromatography column in a first position and to thermally couple to the exit section of the chromatography column in a second position, the second heating device configured to comprise a different temperature than a temperature of the heating device during the chromatographic separation.

In another aspect, a system configured to receive a non-electrically conductive chromatography column in a column space and provide a thermal gradient to the non-electrically conductive chromatography column positioned in the column space during a chromatographic separation, the system comprises a heating device comprising a body configured to thermally couple to an inlet section of the non-electrically conductive chromatography column, the body comprising an outer surface that is configured to contact at least an inner surface of the inlet section of the non-electrically conductive chromatography column to thermally couple the heating device to the inlet section of the non-electrically conductive chromatography column, a motor coupled to the heating device and configured to provide longitudinal movement of the heating device along the non-electrically conductive chromatography column, and a processor electrically coupled to the motor and configured to control the motor and the longitudinal movement of the heating device from the inlet section of the non-electrically conductive chromatography column toward an exit section of the non-electrically conductive chromatography column during a chromatographic separation using the heating device to provide a thermal gradient to the non-electrically conductive chromatography column during the chromatographic separation.

In certain examples, the system comprises an AC power source electrically coupled to the motor and the processor. In other examples, the system comprises a DC power source electrically coupled to the motor and the processor, e.g., at least one of an electrochemical cell, a fuel cell, a solar cell or a wind turbine configured to provide a direct current. In other configurations, the system comprises a display electrically coupled to the processor. In certain examples, the motor is configured as a stepper motor. In some embodiments, the system comprises a transmitter electrically coupled to the processor. In certain instances, the transmitter is configured to wirelessly couple to a mobile device. In other examples, the transmitter comprises at least one of a Bluetooth device, a near field communication device, a WLAN device, a USB device, a RF device, a cellular device, a radio device, a satellite device, or a GPS device. In some embodiments, the system comprises an oven configured to thermally couple to the chromatography column and to receive the heating device and the chromatography column. In certain instances, the oven is configured to operate at a substantially constant temperature during the chromatographic separation. In other configurations, the heating device is the only heating device present in the chromatography system to provide heat to the chromatography column. In some embodiments, the system comprises a cooling device thermally coupled to the heating device and configured to assist in providing the thermal gradient to the chromatography column, e.g., the cooling device can be configured as one or more of a fan, a Peltier cooler, a cooling rod and a heatsink. In some examples, the heating device and the cooling device together are configured to provide a linear thermal gradient along a longitudinal dimension of the chromatography column from the inlet section to the exit section. In other embodiments, the system comprises a detector configured to fluidically couple to the chromatography column. In certain instances, the heating device is configured as a cylindrical jacket that contacts inner surfaces of the inlet section of the chromatography column. In some examples, the heating device is sized and arranged to contact inner coil surfaces of a capillary column coil to provide the thermal gradient to the capillary column. In some embodiments, the heating device is configured to thermally couple to two or more chromatography columns during the chromatographic separation to provide a temperature gradient to each of the two or more chromatography columns. In other examples, the system comprises a second heating device configured to thermally couple to the inlet section of the chromatography column in a first position and to thermally couple to the exit section of the chromatography column in a second position, the second heating device configured to comprise a different temperature than a temperature of the heating device during the chromatographic separation In an additional aspect, a chromatography system comprises a heating device configured to thermally couple to and contact a section of a chromatography column at a first position that is less than an overall length of the chromatography column, and a motor coupled to the heating device and configured to control longitudinal movement of the heating device along the chromatography column from the first position to a second position different from the first position during a chromatographic separation using the heating device to provide a thermal gradient to the chromatography column during the chromatographic separation.

In certain examples, the system comprises a processor configured to control the motor and longitudinal movement of the heating device during the chromatographic separation. In other embodiments, the system comprises an AC power source or a DC power source electrically coupled to the processor. In certain instances, the DC power source comprises at least one of an electrochemical cell, a fuel cell, a solar cell or a wind turbine configured to provide a direct current. In other examples, the system comprises a display electrically coupled to the processor. In some embodiments, the motor is configured as a stepper motor. In certain examples, the system comprises a transmitter electrically coupled to the processor. In some instances, the transmitter is configured to wirelessly couple to a mobile device. In certain examples, the transmitter comprises at least one of a Bluetooth device, a near field communication device, a WLAN device, a USB device, a RF device, a cellular device, a radio device, a satellite device, or a GPS device. In some embodiments, the system comprises an oven configured to thermally couple to the chromatography column and to receive the heating device and the chromatography column. In other examples, the oven is configured to operate at a substantially constant temperature during the chromatographic separation. In some embodiments, the heating device is the only heating device present in the chromatography system to provide heat to the chromatography column. In certain configurations, the system comprises a cooling device thermally coupled to the heating device and configured to assist in providing the thermal gradient to the chromatography column. In some examples, the cooling device is configured as one or more of a fan, a Peltier cooler, a cooling rod and a heat sink. In other examples, the heating device and the cooling device together are configured to provide a linear thermal gradient along a longitudinal dimension of the chromatography column from the first position to the second position. In some embodiments, the system comprises a detector configured to fluidically couple to the chromatography column. In other embodiments, the heating device is configured as a cylindrical jacket that contacts inner coil surfaces of the inlet section of the chromatography column. In some examples, the heating device is sized and arranged to contact inner coil surfaces of a capillary column coil to provide the thermal gradient to the capillary column. In some embodiments, the heating device is configured to thermally couple to two or more chromatography columns during the chromatographic separation to provide a temperature gradient to each of the two or more chromatography columns. In other configurations, the system comprises a second heating device configured to thermally couple to and contact the section of a chromatography column at a first position that is less than an overall length of the chromatography column, the second heating device configured to comprise a different temperature than a temperature of the heating device during the chromatographic separation.

In another aspect, a kit comprises a heating device configured to thermally couple to a chromatography column at a first position, and instructions for using the heating device with the chromatography column to provide a thermal gradient to the chromatography column during a chromatographic separation by moving the heating device in a longitudinal direction along the chromatography column from the first position to a second position different from the first position.

In certain configurations, the kit comprises a motor configured to couple to the heating device to move the heating device in the longitudinal direction. In other configurations, the motor is a stepper motor. In some embodiments, the kit comprises a processor configured to electrically couple to the motor and control movement of the heating device in the longitudinal direction. In some examples, the kit comprises a chromatography column configured for use with the heating device. In some examples, the chromatography column is selected from the group consisting of a coiled capillary column, a coiled capillary column bundle, a wafer column and a non-coiled capillary column. In other examples, the kit comprises a DC power source. In some embodiments, the DC power source comprises at least one of an electrochemical cell, a fuel cell, a solar cell or a wind turbine configured to provide a direct current. In some instances, the kit comprises a detector. In some embodiments, the kit comprises a second DC power source different from the DC power source.

In another aspect, a method comprises providing a heating device configured to thermally couple to a chromatography column at an inlet section of the chromatography column in a first position and to thermally couple to the chromatography column at a section downstream from the inlet section in a second position, the heating device configured to move in a longitudinal dimension along the chromatography column from the first position to the second position during a chromatographic separation to provide a thermal gradient during the chromatographic separation.

In certain instances, the method comprises providing a substantially linear thermal gradient during the chromatographic separation by maintaining the heating device at a substantially constant temperature during the chromatographic separation. In other instances, the method comprises providing a substantially linear thermal gradient during the chromatographic separation using a cooling device thermally coupled to the heating device. In some embodiments, the method comprises moving the cooling device during the chromatographic separation. In certain examples, the method comprises maintaining the cooling device in a stationary position during the chromatographic separation. In some instances, the method comprises moving the heating device from the first position to the second position using a motor coupled to the heating device. In some embodiments, the method comprises providing power to the motor using a DC power source electrically coupled to the motor. In certain examples, the method comprises providing a non-linear thermal gradient using the heating device. In some examples, the method comprises configuring the chromatography system with a processor. In certain embodiments, the method comprises configuring the processor to wirelessly couple to a mobile device that receives chromatography information from the system during the chromatographic separation.

In another aspect, a method of performing gas chromatography comprises providing a heating device configured to thermally couple to inner coil surfaces of a section of a chromatography column coil in a first position of the heating device and configured to thermally couple to inner surfaces of a different section of the chromatography column coil in a second position, the heating device configured to move from the first position to the second position to provide a thermal gradient during a gas chromatographic separation.

In some instances, the method comprises providing a cooling device configured to thermally couple to the heating device, the heating device and cooling device together configured to provide a substantially linear thermal gradient during the gas chromatographic separation. In other instances, the method comprises providing the substantially linear thermal gradient during the chromatographic separation by maintaining one end of the heating device at a substantially constant temperature during the chromatographic separation. In certain examples, the method comprises moving the cooling device during the chromatographic separation. In some embodiments, the method comprises maintaining the cooling device in a stationary position during the chromatographic separation. In some examples, the method comprises moving the heating device from the first position to the second position using a motor coupled to the heating device. In certain examples, the method comprises providing power to the motor using a DC power source electrically coupled to the motor. In some examples, the method comprises providing a non-linear thermal gradient using the heating device. In certain examples, the method comprises configuring the chromatography system with a processor. In some embodiments, the method comprises configuring the processor to wirelessly couple to a mobile device that receives chromatography information from the system during the chromatographic separation.

In an additional aspect, a method of separating two or more analytes using a thermal gradient comprises providing a heating device configured to thermally couple to a chromatography column in a column space of a chromatography system, in which the heating device is configured to thermally couple to the inlet section of the chromatography column in a first position and to thermally couple to a section of the chromatography column downstream of the inlet section in a second position, and providing instructions for moving the heating device in a longitudinal direction of the chromatography column from the first position to the second position to provide a thermal gradient to the chromatography column during a chromatographic separation.

In certain examples, the method comprises providing a chromatography column configured to receive the heating device in an inner space formed by coiling of the chromatography column. In some embodiments, the method comprises providing a motor configured to couple to the heating device to control movement of the heating device in the longitudinal direction. In other examples, the method comprises providing a cooling device configured to thermally couple to a section of the chromatography column other than a section where the heating device is thermally coupled, in which the heating device and cooling device together are configured to provide a substantially linear thermal gradient during chromatographic separation using the chromatography column. In some instances, the method comprises configuring the cooling device as a fan.

In another aspect, a portable chromatography system comprises a housing sized and arranged to permit carrying of the system by a human, the housing comprising, an injector, a column space configured to receive a chromatography column that fluidically couples to the injector to provide sample injected into the injector to an inlet section of the chromatography column, a heating device configured to thermally couple to the chromatography column in the column space, in which the heating device is configured to thermally couple to the inlet section of the chromatography column in a first position and to thermally couple to a section of the chromatography column downstream of the inlet section in a second position, in which the heating device is configured to move in a longitudinal direction of the chromatography column from the first position to the second position to provide a thermal gradient during chromatographic separation using the heating device, a detector configured to fluidically couple to the chromatography column at an exit end of the chromatography column to receive analyte from the chromatography column, and a processor electrically coupled to the detector.

In certain configurations, the system comprises a motor within the housing and coupled to the heating device and electrically coupled to the processor. In other configurations, the system comprises a DC power source electrically coupled to the processor and positioned within the housing. In some embodiments, the DC power source is configured as an electrochemical cell, a fuel cell, a solar cell or a wind turbine configured to provide a direct current. In other instances, the heating device is configured to thermally couple to a column that is one or more of a capillary column, a capillary column bundle and a wafer column.

In another aspect, a chromatography system comprises a heating device configured to thermally couple to an inlet section of a chromatography column in a first position and to thermally couple to an exit section of a chromatography column in a second position, and a processor configured to control movement of the chromatography column from the first position to the second position during the chromatographic separation using the heating device to provide a thermal gradient to the chromatography column during the chromatographic separation.

In certain configurations, the system comprises a motor coupled to the chromatography column device and electrically coupled to the processor, the motor configured to move the chromatography column from the first position to the second position. In other configurations, the system comprises a DC power source electrically coupled to the processor. In some embodiments, the DC power source comprises at least one of an electrochemical cell, a fuel cell, a solar cell or a wind turbine configured to provide a direct current. In certain examples, the system comprises a display electrically coupled to the processor. In other examples, the motor is configured as a stepper motor. In some embodiments, the system comprises a transmitter electrically coupled to the processor. In certain examples, the transmitter is configured to wirelessly couple to a mobile device. In some examples, the transmitter comprises at least one of a Bluetooth device, a near field communication device, a WLAN device, a USB device, a RF device, a cellular device, a radio device, a satellite device, or a GPS device. In certain embodiments, the system comprises an oven configured to thermally couple to the chromatography column and to receive the heating device and the chromatography column. In other embodiments, the oven is configured to operate at a substantially constant temperature during the chromatographic separation. In some examples, the heating device is the only heating device present in the chromatography system to provide heat to the chromatography column. In other examples, the system comprises a cooling device thermally coupled to the heating device and the chromatography column, the cooling device configured to assist in providing the thermal gradient to the chromatography column. In some embodiments, the cooling device is configured as one or more of a fan, a Peltier cooler, a cooling rod and a heatsink. In certain examples, the heating device and the cooling device together are configured to provide a linear thermal gradient along a longitudinal dimension of the chromatography column from the inlet section to the exit section. In some embodiments, the system comprises a detector configured to fluidically couple to the chromatography column. In some examples, the system comprises a motor coupled to the heating device, the motor configured to move the heating device during movement of the chromatography column. In other examples, the heating device is sized and arranged to receive and contact surfaces of chromatography column to provide the thermal gradient to the chromatography column. In some examples, the heating device is configured to thermally couple to two or more chromatography columns during the chromatographic separation to provide a temperature gradient to each of the two or more chromatography columns. In certain embodiments, the system comprises a second heating device configured to thermally couple to the inlet section of the chromatography column in a first position and to thermally couple to the exit section of the chromatography column in a second position, the second heating device configured to comprise a different temperature than a temperature of the heating device during the chromatographic separation.

In an additional aspect, a system configured to receive a non-electrically conductive chromatography column in a column space and provide a thermal gradient to the non-electrically conductive chromatography column positioned in the column space during a chromatographic separation comprises a heating device comprising a body configured to thermally couple to an inlet section of the non-electrically conductive chromatography column, the body comprising an outer surface that is configured to contact at least an inner coil surface of the inlet section of the non-electrically conductive chromatography column coil to thermally couple the heating device to the inlet section of the non-electrically conductive chromatography column coil, a motor configured to couple to the non-electrically conductive chromatography column coil to provide longitudinal movement of the non-electrically conductive chromatography column coil along the heating device, and a processor electrically coupled to the motor and configured to control the motor and the longitudinal movement of the non-electrically conductive chromatography column coil from the inlet section of the non-electrically conductive chromatography column coil toward an exit section of the non-electrically conductive chromatography column coil during a chromatographic separation using the heating device to provide a thermal gradient to the non-electrically conductive chromatography column coil during the chromatographic separation. If desired, the system can be configured for use with non-coil columns as well.

In certain configurations, the system comprises an AC power source electrically coupled to the motor and the processor. In some embodiments, the system comprises a DC power source electrically coupled to the motor and the processor. In certain examples, the DC power source comprises at least one of an electrochemical cell, a fuel cell, a solar cell or a wind turbine configured to provide a direct current. In other examples, the system comprises a display electrically coupled to the processor. In some embodiments, the motor is configured as a stepper motor. In certain embodiments, the system comprises a transmitter electrically coupled to the processor. In other embodiments, the transmitter is configured to wirelessly couple to a mobile device. In some examples, the transmitter comprises at least one of a Bluetooth device, a near field communication device, a WLAN device, a USB device, a RF device, a cellular device, a radio device, a satellite device, or a GPS device. In certain configurations, the system comprises an oven configured to thermally couple to the chromatography column coil and to receive the heating device and the chromatography column coil. In other configurations, the oven is configured to operate at a substantially constant temperature during the chromatographic separation. In some embodiments, the heating device is the only heating device present in the chromatography system to provide heat to the chromatography column. In other embodiments, the system comprises a cooling device thermally coupled to the heating device and configured to assist in providing the thermal gradient to the chromatography column coil. In certain examples, the cooling device is configured as one or more of a fan, a Peltier cooler, a cooling rod and a heatsink. In some instances, the heating device and the cooling device together are configured to provide a linear thermal gradient along a longitudinal dimension of the chromatography column coil from the inlet section to the exit section. In other instances, the system comprises a detector configured to fluidically couple to the chromatography column. In some embodiments, the system comprises a second motor coupled to the heating device, the motor configured to move the heating device during movement of the chromatography column coil. In certain examples, the heating device is sized and arranged to contact inner coil surfaces of a capillary column coil to provide the thermal gradient to the capillary column coil. In some examples, the heating device is configured to thermally couple to two or more chromatography columns during the chromatographic separation to provide a temperature gradient to each of the two or more chromatography columns. In certain configurations, the system comprises a second heating device configured to thermally couple to the inlet section of the chromatography column in a first position and to thermally couple to the exit section of the chromatography column in a second position, the second heating device configured to comprise a different temperature than a temperature of the heating device during the chromatographic separation.

In another aspect, a chromatography system comprises a heating device configured to thermally couple to and contact a section of a chromatography column at a first position that is less than an overall length of the chromatography column, and a motor configured to couple to the chromatography column and configured to control longitudinal movement of the chromatography column along the heating device from the first position to a second position different from the first position during a chromatographic separation using the heating device to provide a thermal gradient to the chromatography column during the chromatographic separation.

In some examples, the system comprises a processor configured to control the motor and longitudinal movement of the chromatography column during the chromatographic separation. In certain instances, the system comprises a DC power source electrically coupled to the processor. In some examples, the DC power source comprises at least one of an electrochemical cell, a fuel cell, a solar cell or a wind turbine configured to provide a direct current. In other examples, the system comprises a display electrically coupled to the processor. In some configurations, the motor is configured as a stepper motor. In other examples, the system comprises a transmitter electrically coupled to the processor. In some examples, the transmitter is configured to wirelessly couple to a mobile device. In other instances, the transmitter comprises at least one of a Bluetooth device, a near field communication device, a WLAN device, a USB device, a RF device, a cellular device, a radio device, a satellite device, or a GPS device. In some examples, the system comprises an oven configured to thermally couple to the chromatography column and to receive the heating device and the chromatography column. In some embodiments, the oven is configured to operate at a substantially constant temperature during the chromatographic separation. In other examples, the heating device is the only heating device present in the chromatography system to provide heat to the chromatography column. In some configurations, the system comprises a cooling device thermally coupled to the heating device and configured to assist in providing the thermal gradient to the chromatography column. In other instances, the cooling device is configured as one or more of a fan, a Peltier cooler, a cooling rod and a heat sink. In some embodiments, the heating device and the cooling device together are configured to provide a linear thermal gradient along a longitudinal dimension of the chromatography column from the first position to the second position. In some examples, the system comprises a detector configured to fluidically couple to the chromatography column. In other examples, the system comprises a second motor coupled to the heating device, the second motor configured to move the heating device during movement of the chromatography column. In some embodiments, the heating device is sized and arranged to contact inner coil surfaces of a capillary column coil to provide the thermal gradient to the capillary column coil. In other configurations, the heating device is configured to thermally couple to two or more chromatography columns during the chromatographic separation to provide a temperature gradient to each of the two or more chromatography columns. In some embodiments, the system comprises a second heating device configured to thermally couple to and contact the section of a chromatography column at a first position that is less than an overall length of the chromatography column, the second heating device configured to comprise a different temperature than a temperature of the heating device during the chromatographic separation.

In an additional aspect, a kit comprises a heating device configured to thermally couple to a chromatography column at a first position, and instructions for using the heating device with the chromatography column to provide a thermal gradient to the chromatography column during a chromatographic separation by moving the chromatography column in a longitudinal direction along the heating device from the first position to a second position different from the first position.

In some instances, the kit comprises a motor configured to couple to the chromatography column to move the chromatography column in the longitudinal direction. In other instances, the motor is a stepper motor. In some examples, the kit comprises a processor configured to electrically couple to the motor and control movement of the chromatography column in the longitudinal direction. In some embodiments, the kit comprises a chromatography column configured for use with the heating device. In certain examples, the chromatography column is selected from the group consisting of a coiled capillary column, a coiled capillary column bundle, a wafer column and a non-coiled capillary column. In some embodiments, the kit comprises a DC power source. In some examples, the DC power source comprises at least one of an electrochemical cell, a fuel cell, a solar cell or a wind turbine configured to provide a direct current. In some instances, the kit comprises a detector. In other examples, the kit comprises a second DC power source different from the DC power source.

In another aspect, a method comprises providing a heating device configured to thermally couple to a chromatography column at an inlet section of the chromatography column in a first position and to thermally couple to the chromatography column at a section downstream from the inlet section in a second position, the heating device configured to receive the chromatography column during movement of the chromatography column in a longitudinal dimension along the heating device from the first position to the second position during a chromatographic separation to provide a thermal gradient to the chromatography column during the chromatographic separation.

In certain examples, the method comprises providing a substantially linear thermal gradient during the chromatographic separation by maintaining the heating device at a substantially constant temperature during the chromatographic separation. In other examples, the method comprises providing a substantially linear thermal gradient during the chromatographic separation using a cooling device thermally coupled to the heating device. In some embodiments, the method comprises moving the cooling device during the chromatographic separation. In certain examples, the method comprises maintaining the cooling device in a stationary position during the chromatographic separation. In some instances, the method comprises moving the chromatography column from the first position to the second position using a motor coupled to the chromatography column. In some embodiments, the method comprises providing power to the motor using a DC power source electrically coupled to the motor. In certain examples, the method comprises providing a non-linear thermal gradient using the heating device. In other examples, the method comprises configuring the chromatography system with a processor. In some examples, the method comprises configuring the processor to wirelessly couple to a mobile device that receives chromatography information from the system during the chromatographic separation.

In an additional aspect, a method of performing gas chromatography comprises providing a heating device configured to thermally couple to inner coil surfaces of a section of a chromatography column coil in a first position of the heating device and configured to thermally couple to inner coil surfaces of a different section of the chromatography column coil in a second position, the heating device configured to receive the chromatography column coil during movement of the chromatography column coil from the first position to the second position to provide a thermal gradient to the chromatography column coil during a gas chromatographic separation.

In certain examples, the method comprises providing a cooling device configured to thermally couple to the heating device, the heating device and cooling device together configured to provide a substantially linear thermal gradient during the gas chromatographic separation. In other examples, the method comprises providing the substantially linear thermal gradient during the chromatographic separation by maintaining one end of the heating device at a substantially constant temperature during the chromatographic separation. In some instances, the method comprises moving the cooling device during the chromatographic separation. In other examples, the method comprises maintaining the cooling device in a stationary position during the chromatographic separation. In certain instances, the method comprises moving the chromatography column coil from the first position to the second position using a motor coupled to the heating device. In other examples, the method comprises providing power to the motor using a DC power source electrically coupled to the motor. In certain examples, the method comprises providing a non-linear thermal gradient using the heating device. In some embodiments, the method comprises configuring the chromatography system with a processor. In some instances, the method comprises configuring the processor to wirelessly couple to a mobile device that receives chromatography information from the system during the chromatographic separation.

In another aspect, a method of separating two or more analytes using a thermal gradient, comprises providing a heating device configured to thermally couple to a chromatography column in a column space of a chromatography system, in which the heating device is configured to thermally couple to the inlet section of the chromatography column in a first position and to thermally couple to a section of the chromatography column downstream of the inlet section in a second position, and providing instructions for moving the chromatography column in a longitudinal direction of the chromatography column from the first position to the second position to provide a thermal gradient to the chromatography column during a chromatographic separation.

In certain examples, the method comprises providing a chromatography column configured to receive the heating device in an inner space formed by coiling of the chromatography column. In some embodiments, the method comprises providing a motor configured to couple to the chromatography column to control movement of the chromatography column in the longitudinal direction. In certain examples, the method comprises providing a cooling device configured to thermally couple to a section of the chromatography column other than a section where the heating device is thermally coupled, in which the heating device and cooling device together are configured to provide a substantially linear thermal gradient during chromatographic separation using the chromatography column. In some embodiments, the method comprises configuring the cooling device as a fan.

In another aspect, a portable chromatography system comprises a housing sized and arranged to permit carrying of the system by a human, the housing comprising an injector, a column space configured to receive a chromatography column that fluidically couples to the injector to provide sample injected into the injector to an inlet section of the chromatography column, a heating device configured to thermally couple to the chromatography column in the column space, in which the heating device is configured to thermally couple to the inlet section of the chromatography column in a first position and to thermally couple to a section of the chromatography column downstream of the inlet section in a second position, in which the heating device is configured to receive the chromatography column during movement of the chromatography column in a longitudinal direction from the first position to the second position to provide a thermal gradient during chromatographic separation using the heating device, a detector configured to fluidically couple to the chromatography column at an exit end of the chromatography column to receive analyte from the chromatography column, and a processor electrically coupled to the detector.

In some examples, the system comprises a motor within the housing and coupled to the chromatography column and electrically coupled to the processor. In other examples, the system comprises a DC power source electrically coupled to the processor and positioned within the housing. In certain examples, the DC power source is configured as an electrochemical cell, a fuel cell, a solar cell or a wind turbine configured to provide a direct current. In some examples, the heating device is configured to thermally couple to a column that is one or more of a capillary column, a capillary column bundle and a wafer column.

In another aspect, a method comprises providing a first heating device and a second heating device each configured to thermally couple to a chromatography column at an inlet section of the chromatography column in a first position and to thermally couple to the chromatography column at a section downstream from the inlet section in a second position, each of the first heating device and the second heating device configured to move in a longitudinal dimension along the chromatography column from the first position to the second position during a chromatographic separation to provide a thermal gradient during the chromatographic separation, in which the first heating device is configured to thermally couple to the column for a first period and the second heating device is configured to thermally couple to the column after the first period once the first heating device has been thermally decoupled from the column.

In certain examples, the method comprises providing a substantially linear thermal gradient during the chromatographic separation by maintaining the first and second heating devices at a substantially constant temperature during the chromatographic separation. In other examples, the method comprises providing a substantially linear thermal gradient during the chromatographic separation using a cooling device thermally coupled to at least one of the first and second heating devices. In some examples, the method comprises moving the cooling device during the chromatographic separation. In certain embodiments, the method comprises maintaining the cooling device in a stationary position during the chromatographic separation. In some examples, the method comprises moving each of the first and second heating devices from the first position to the second position using a motor coupled to the heating device. In certain examples, the method comprises providing power to the motor using a DC power source electrically coupled to the motor. In some embodiments, the method comprises providing a non-linear thermal gradient using the first and second heating devices. In certain embodiments, the method comprises configuring the chromatography system with a processor. In other instances, the method comprises configuring the processor to wirelessly couple to a mobile device that receives chromatography information from the system during the chromatographic separation.

In an additional aspect, a method of performing gas chromatography comprises providing a first heating device and a second heating device each configured to thermally couple to inner coil surfaces of a section of a chromatography column coil in a first position of each of the first and second heating devices and configured to thermally couple to inner coil surfaces of a different section of the chromatography column coil in a second position, the first and second heating devices configured to move from the first position to the second position to provide a thermal gradient during a gas chromatographic separation, in which the first heating device is configured to thermally couple to the section for a first period and the second heating device is configured to thermally couple to the section after the first period and once the first heating device has been thermally decoupled from the section.

In certain configurations, the method comprises providing a cooling device configured to thermally couple to one of the first and second heating devices, the first and second heating devices and the cooling device together configured to provide a substantially linear thermal gradient during the gas chromatographic separation. In other examples, the method comprises providing the substantially linear thermal gradient during the chromatographic separation by maintaining one end of the first and second heating devices at a substantially constant temperature during the chromatographic separation. In some examples, the method comprises moving the cooling device during the chromatographic separation. In some embodiments, the method comprises maintaining the cooling device in a stationary position during the chromatographic separation. In other examples, the method comprises moving the first and second heating devices from the first position to the second position using a motor coupled to the first and second heating devices. In certain instances, the method comprises providing power to the motor using a DC power source electrically coupled to the motor. In some embodiments, the method comprises providing a non-linear thermal gradient using the first and second heating devices. In certain examples, the method comprises configuring the chromatography system with a processor. In other examples, the method comprises configuring the processor to wirelessly couple to a mobile device that receives chromatography information from the system during the chromatographic separation.

Additional features, aspect, examples, configurations and embodiments are described in more detail below.

BRIEF DESCRIPTION OF THE FIGURES

Certain embodiments are described with reference to the accompanying figures in which:

FIGS. 1A-6B are illustrations showing a heating device, column and a thermal gradient as the heating device is moved along a longitudinal dimension of the column, in accordance with certain examples;

FIG. 11 is another illustration of a heating device configured for use with a wafer column, in accordance with certain examples;

FIG. 12 is an illustration of a heating device comprising apertures at one end of the heating device, in accordance with certain configurations;

FIG. 16A is an illustration of a chromatography system comprising a motor, a heating device and a chromatography column, in accordance with certain examples;

FIG. 16B is an illustration of a chromatography system comprising a processor, a motor, a heating device and a chromatography column, in accordance with certain examples;

Figure 2A:
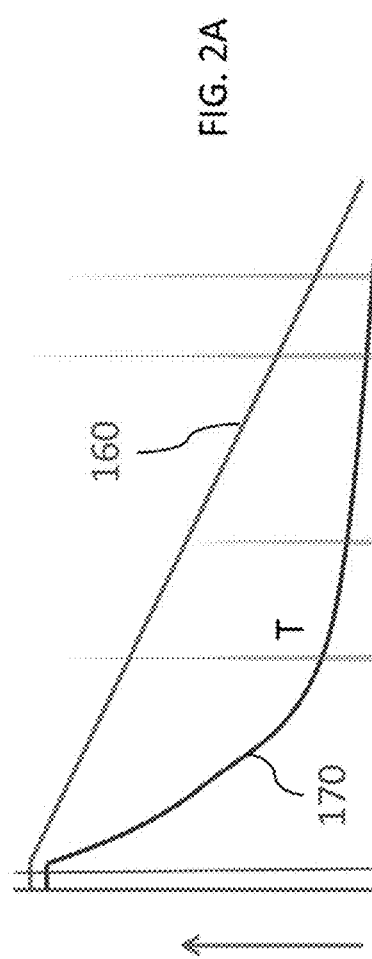

It will be recognized by the person of ordinary skill in the art, given the benefit of this disclosure, that certain dimensions or features in the figures may have been enlarged, distorted or shown in an otherwise unconventional or non-proportional manner to provide a more user friendly version of the figures. No particular length, diameter or thickness, is intended by the depictions in the figures, and relative sizes of the figure components are not intended to limit the sizes of any of the components in the figures. Where dimensions or values are specified in the description below, the dimensions or values are provided for illustrative purposes only.

DETAILED DESCRIPTION

Certain embodiments are described below with reference to singular and plural terms in order to provide a more user friendly description of the technology disclosed herein. These terms are used for convenience purposes only and are not intended to limit the chromatography systems, heating devices and their use as including or excluding certain features unless otherwise noted as being present in a particular embodiment described herein. Certain devices are described herein as being thermally coupled to each other. Thermal coupling refers to the ability of heat to transfer from one component to another component. Other components herein may be fluidically coupled to each other, which refers to the ability of a fluid such as a liquid or gas being able to flow from one component to another component. The chromatography devices described herein may be configured to receive a liquid or gas sample (or both) and separate components in the sample using a chromatography column and the heating device.

In certain configurations of the devices and systems described herein, a heating device or heater may be present to provide a temperature gradient. The heating device need not be the only heating device present, and in many configurations, the heating device is configured as a secondary heating device that can provide a thermal gradient. For example, the device or system may comprise a first heating device such as an oven to provide a substantially constant temperature and can include a second heating device that can provide a thermal gradient. The heating device that provides the thermal gradient may be configured as a low power device to permit the devices and system including the heating device to be portable and/or use power from DC power sources such as batteries, fuel cells, wind generators and/or photovoltaic cells.

In some instances, the exact nature of the thermal gradient provided by the heating device may vary. In certain configurations, the heating device can be configured to move or translate along another device, e.g., a column. For example, a column can be placed within the heating device, the heating device can be placed within an inner space formed by the column, the heating device can be placed adjacent to a column or the heating device may otherwise be thermally coupled to the column such that a thermal gradient exists in the portion of the column thermally coupled to the heating device. In some configurations, one end of the heating device may comprise a higher temperature than another end of the heating device to provide the thermal gradient. For example, a fan, heatsink Peltier cooler, a cooling rod or the like can be thermally coupled or physically contact one end of the heating device to provide a temperature different from one end of the heating device to the other end of the heating device. The thermal gradient may be linear, non-linear or may take other forms or shapes as desired. The exact speed in which the heating device is moved from one portion of a column to another portion of a column (or vice versa when the column is moved) can vary and may assist in controlling the shape of the thermal gradient. In some embodiments, the heating device may be in direct contact with one or more surfaces of a column, whereas in other examples a small air gap or other intervening material or gas may be present between the heating device and the column surface. Where the column takes the form of a coil, the heating device may be moved through the inner space formed by the coil from an inlet section of the coiled column toward an outlet section of the coiled column. This longitudinal movement of the heating device from an inlet section toward an outlet section incrementally provides a thermal gradient to different sections of the coiled column. In certain instances, the heating device may take the form of one or more cylinders that can be moved along the longitudinal axis of the heating device and into and/or out of a coiled column. As noted herein, the coiled column typically resides in oven that provides for temperature control during a chromatographic separation.

To illustrate the basic operation of the heating device, FIGS. 1A-6B illustrate movement of a heating device from an inlet section of a column toward an outlet section of a column. Referring to FIG. 1B, a device is shown that comprises a heating device 110 and a column 120 surrounded by insulation or an insulating member 130. The column 120 is shown in a side view and typically is coiled to decrease the overall column space that the column will occupy. For example, the overall length of the column 120 may be 1 meter or more, 10 meters or more, etc., and coiling of the column 120 can reduce the overall space within the device or system including the column 120. The column 120 comprises an inlet or inlet section 122 and an exit or exit section 124. The inlet section 122 is typically fluidically coupled to an injector or other sample introduction device (not shown) to permit sample to be introduced into the column 120. The exit section 124 may be fluidically coupled to a detector (not shown) to provide separated analyte components to the detector for detection. The heating device 110 and column 120 typically are present within an oven (not shown) to maintain the column 120 at a substantially constant temperature, though the oven temperature can be adjusted during the separation if desired. Referring to FIG. 1A, the temperature of the heating device along the length of the heating device is shown using curve 160 and the temperature of the column along the length of the column is shown using curve 170 at an initial or starting position of the heating device 110. As shown in curve 160, the heating device 110 has a thermal gradient from one side of the heating device 110 to the other. For example, the temperature of the heating device near an end 112 can be higher than the temperature of the heating device 110 near an opposite end 114. In some instances, the temperature of the heating device 110 at the end 114 may be about the same temperature as the oven temperature so that the inlet section 122 of the column 120 is held at about the same temperature as the oven temperature. While a linear thermal gradient is shown in curve 160, if desired the thermal gradient provided by the heating device 110 may be non-linear. Cooling air can be provided in the direction of arrows 150 to keep the temperature of the end 114 of the heating device 110 less than a temperature of the end 112 of the heating device 110. In alternative configurations described below, the temperature of individual sections or portions of the heating device can be controlled to provide a desired thermal gradient. Different analytes components are shown as sandwiched analyte peaks 180 in FIG. 1A with no baseline separation between the different analytes.

In use of the heating device 110, the heating device 110 can be configured as a cylinder that can be inserted into and out of inner space formed by coiling of a capillary column. The heating device 110 can be heated at the end 112 by a rod held at constant temperature (upper temperature limit for the desired separation) or may be heated in other configurations as noted herein. The opposite end of the cylinder can be cooled using the air 150 or using a heatsink, cooling rod or Peltier cooler coupled to the end 114. The combination of the heat and cooling can provide a thermal gradient along the length of the cylinder from the end 112 to the end 114. The longitudinal gaps between each coil of the column 120 can be spaced large to small from the end 122 to the end 124 (see the spaced circles in FIG. 1B) so that a decaying thermal gradient is provided along the length of the column 120. Alternatively, the column coils may be spaced about the same in a longitudinal direction, and the thermal gradient can be provided by differential temperatures from the heating device. A sample can be introduced at the end 122 of the column 120. The sample can be a complex or simple mixture. For this example, there are 4 analytes in the mixture.

Figure 2B:
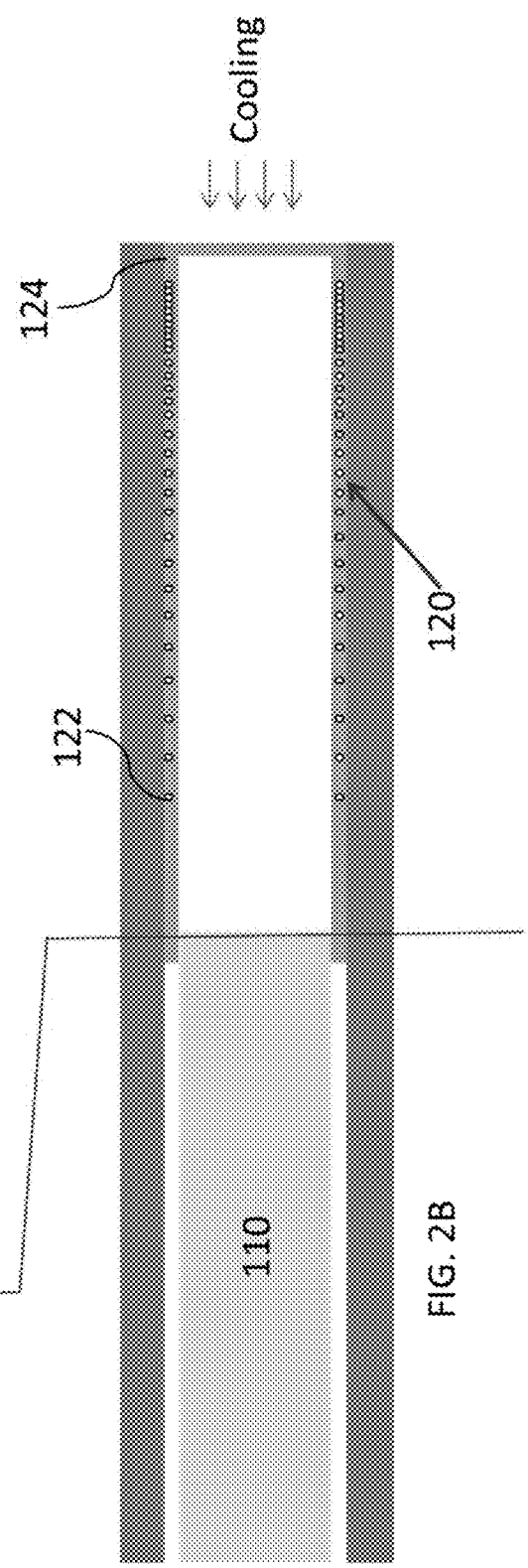
Figure 3A:
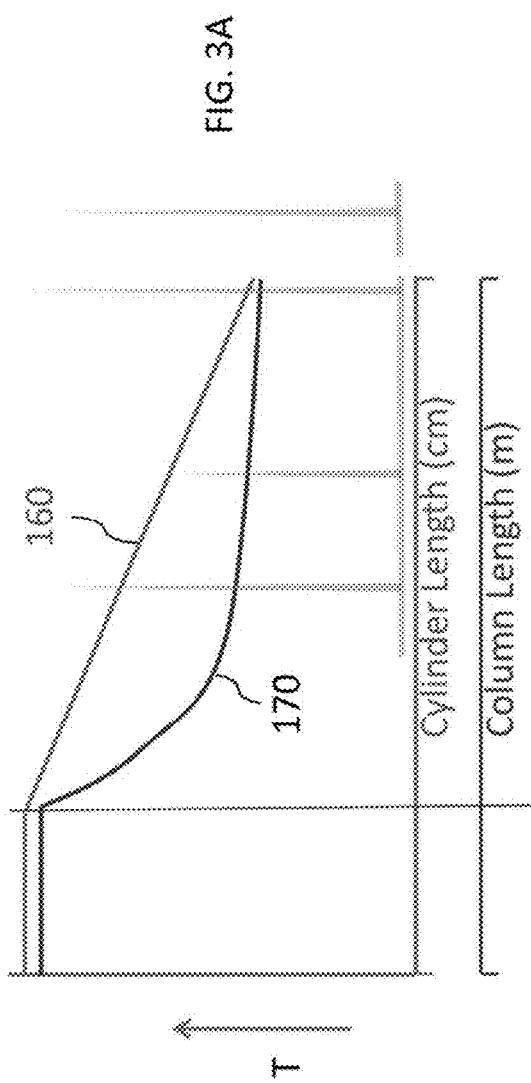
Figure 3B:
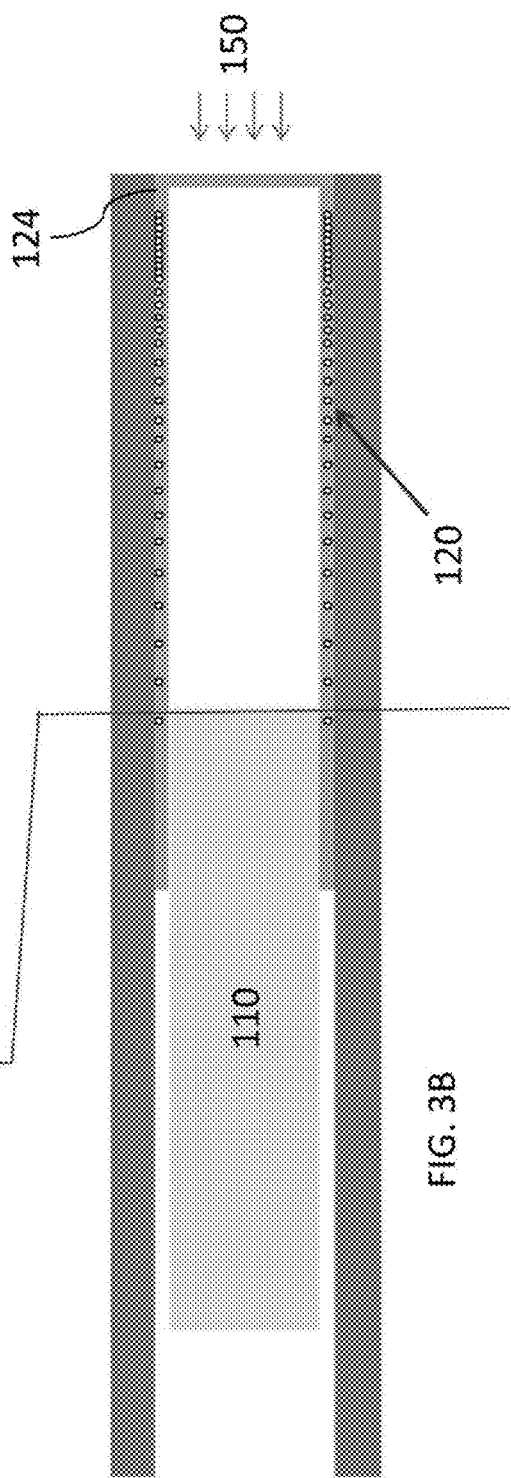

In certain instances, after the sample is introduced to the head 122 of the column 120 the components separate out along the column 120 with the more volatile components traveling further to the end 124 of the column 120 and the less volatile components remaining closer to the inlet end 122 of the column 120 (see FIGS. 2A and 2B). The heating device 110 may then be moved from its initial position and into the inner space of the column 120 to a different position (see FIGS. 3A and 3B). As shown in the curve 170 in FIG. 3A, this movement of the heating device 110 alters the temperature along the length of the column 120. As the heating device 110 is inserted into the column 120, the components on the column 120 experience a higher temperature and are eluted out the end 124 of the column 120 to a detector (not shown) or other component or device. The speed of insertion of the heating device determines, at least in part, the speed of elution.

Referring now to FIGS. 4A-6B, continued insertion of the heating device 110 toward an exit end 124 of the column 120 is shown. As the end 114 of heating device 110 gets closer to the end 124 of the column 120, the temperature of the column 120 increases. Decreased coil spacing at the end 124 of the column 120 causes remaining components to elute quickly. As the heating device 110 nears or becomes adjacent to the end 124 of the column 120, all components in the mixture should have eluted from the column 120. These components are shown as separated analyte peaks in each of FIGS. 4A, 5A and 6A. The heating device 110 can then be moved back to its initial position shown in FIGS. 1B and 2B prior to introduction of another sample into the chromatography device. If desired, the heating device 110 may remain in the position shown in FIG. 6B for some period to assist in elution of any remaining components from the column 120. Further, the temperature of the heating device positioned in FIG. 6B can be increased to assist in elution of any high temperature components still remaining on the column. In an alternative configuration, the heating devices 110 of FIGS. 1A-6B can remain stationary, and the column 120 may instead be moved. Or, in some instances, both the heating device 110 and the column 120 can be moved if desired.

Figure 7:
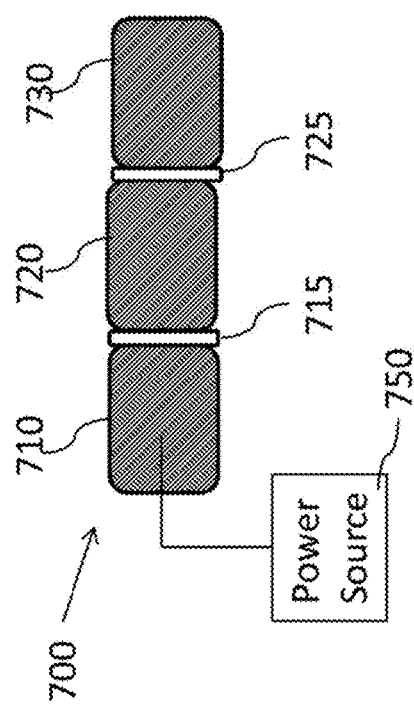
FIG. 7 is an illustration of a heating device comprising different sections, in accordance with certain examples.

In certain configurations, the heating devices described herein may take the form of a cylinder (which can be solid or hollow). The cylinder may be electrically coupled to a power source such that application of a current to the cylinder causes heating of the cylinder. As noted herein, the cylinder may be configured to provide a first temperature at one end and a second temperature, different from the first temperature, at a second end such that a thermal gradient exists between the ends of the cylinder. The differential temperature may be provided, for example, by selectively cooling one end of the cylinder using an air current, heat sink, Peltier cooler, cooling rod or other cooling devices or means. In other instances, the cylinder may comprise individual cylinder sections whose temperatures can be individually regulated. One illustration is shown in FIG. 7. The heating device 700 comprises a generally cylindrical body comprising two or more individual sections such as sections 710, 720, and 730. The sections 710, 720 and 730 can be separated by an insulating material or member, e.g., members 715, 725 such that current applied to one section does not reach another section. The insulators 715, 725 are desirably thick enough to prevent charge transfer between sections 710, 720 and 730 but not so thick so as to create a temperature drop or cold spot between the sections 710, 720 and 730. In the configuration shown in FIG. 7, the electrical couplings between each of the sections 710, 720, 730 and a power source may be present in an interior portion of the sections 710, 720 and 730 so as to not interfere with heat transfer from the sections 710, 720 and 730 to the column (not shown). For example, a power source 750 is shown as electrically coupled to the section 710 through an interior portion of the section 710 to permit movement of the device 700. While not shown, sections 720 and 730 typically comprise their own power source. Alternatively, a resistor network or other devices can be used so that a single power source can be coupled to the various sections, but different amounts of power can be provided to alter the temperature of the various sections 710, 720, 730 of the device 700. In some instances, a sectioned heating device may remain stationary, and the column may instead be moved. In other configurations, the sectioned heating device and the column may both be moved if desired.

In certain embodiments, the heating device used in FIGS. 1A-6B and shown in FIG. 7 can be used to contact inner coil surfaces of a column by inserting the heating device into open inner space formed by coiling of the column. The heating device may physically contact the inner coil surfaces using grooves or other structures in the column or may be positioned close enough to the inner surfaces to transfer heat without the need to physically contact the column. Where physical contact between the heating device and inner surfaces of the column occurs, the friction between the components is not so high as to apply a strain or undue stress on the column. If desired, the heating device may comprise a coating such as a non-stick coating or other slick coatings to reduce friction between the heating device and the inner coil surfaces. In other instances, a thermally conductive track can be placed along and/or in contact with the inner surfaces of the coiled column, and the heating device may ride along the track from an initial position to another position.

Figure 8:
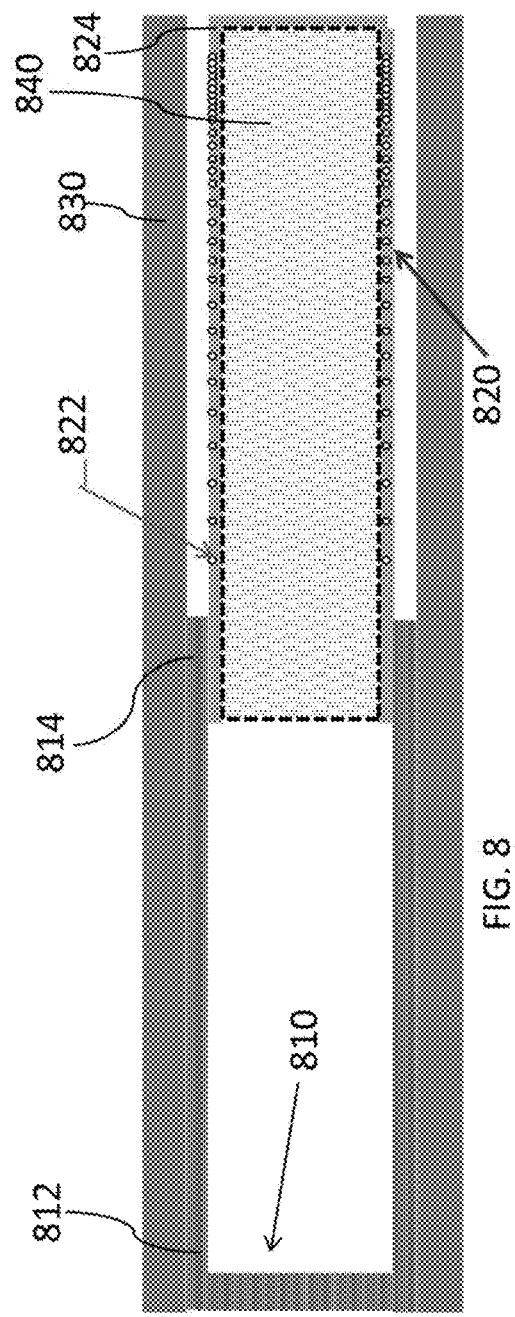
FIG. 8 is an illustration of a heating device configured to contact outer surfaces of a coiled column, in accordance with certain embodiments.

In some embodiments, the heating device may instead be configured to contact an outer surface of the coiled column. For example, the heating device can be configured as a U-shaped member (or C-shaped member depending on the orientation) that can be inserted along the length of the column from an inlet end of the column to an exit end of the column. One illustration is shown in FIG. 8. A heating device 810 comprises a first end 812 and a second end 814. The heating device 810 is configured to contact outer surfaces of a column 820 as the heating device is moved from an inlet end 822 of the column 820 toward an exit end 824 of the column 820. Insulating member 830 is shown that surrounds the heating device 810 and the column 820. If desired, an optional insulating member 840 can be positioned in the inner space formed by the column 820 to reduce any thermal fluctuations caused by open space within the inner space of the coiled column 820. While not shown, air can be blown into the device from the end 824 of the column 820 toward the end 814 of the heating device 810 to provide a difference in temperature between the end 812 and the end 814 of the heating device 810. Alternatively, the heating device 810 may comprise individually controlled sections, e.g., similar to the sections of FIG. 7, to permit temperature control of various sections of the heating device 810. In use of the heating device 810, the heating device 810 can be inserted toward the end 824 of the column 820 in a similar manner as described in connection with FIGS. 1A-6B. The exact speed at which the heating device 810 is inserted may vary depending on the analyte components on the column 820. The heating device 810 can be used to provide a substantially linear thermal gradient or can be used to provide a non-linear gradient. Once the heating device 810 is inserted to a desired final position, the heating device 810 may be moved back to an initial position prior to a subsequent sample injection into the device. While the heating device 810 is described as being moved, the column 820 could instead be moved while the heating device 810 remains stationary. Alternatively, both the column 820 and the heating device 810 can be moved if desired.

Figure 9:
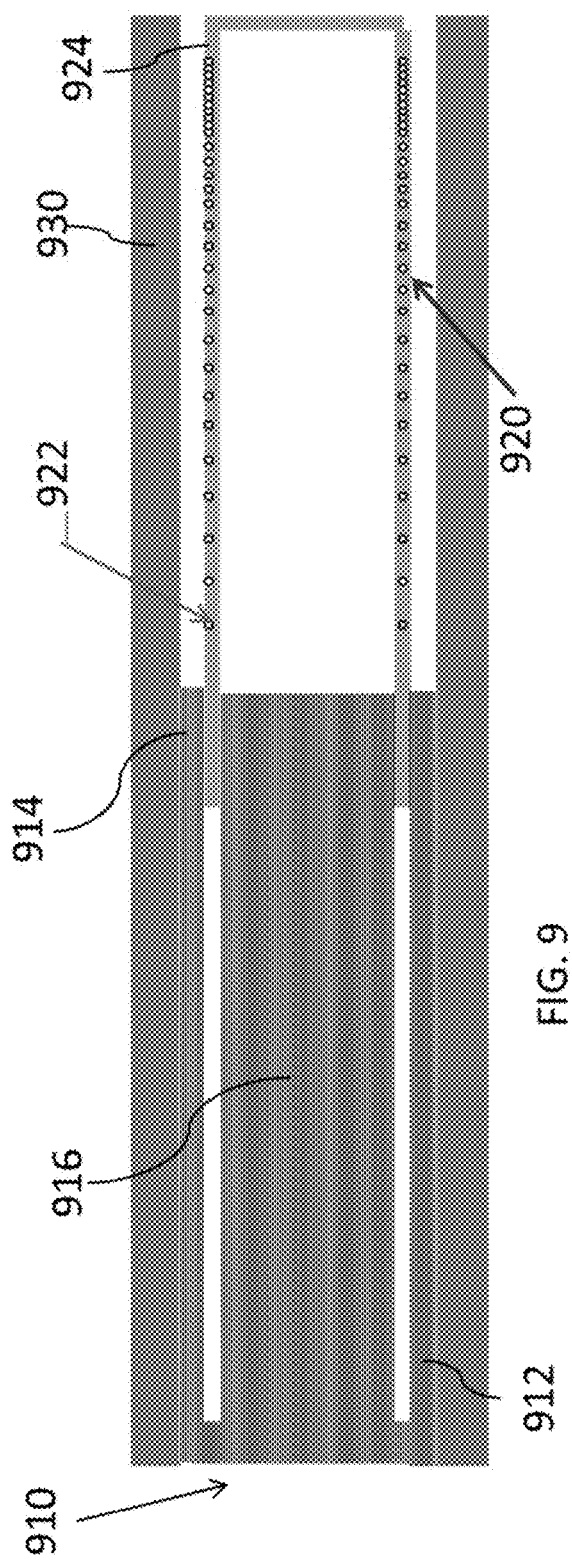
FIG. 9 is an illustration of a heating device configured to contact inner and outer surfaces of a coiled column, in accordance with certain embodiments.

In some instances, it may be desirable to thermally couple the heating device to both the inner and outer surfaces of a coiled column such that no temperature gradients exist or are minimized locally within the column as a result of open space. One configuration is shown in FIG. 9. The heating device 910 comprises arms 912, 914 and an inner body 916. The heating device 910 is configured to contact outer surfaces of a column 920 using the arms 912, 914 and inner surfaces of the column 920 using the body 916 as the heating device 910 is moved from an inlet end 922 of the column 920 toward an exit end 924 of the column 920. Insulating member 930 is shown that surrounds the heating device 910 and the column 920. While not shown, air can be blown into the device from the end 924 of the column 920 toward the end of the heating device 910 to provide a difference in temperature between the ends of the heating device 910. Alternatively, the heating device 910, e.g. the arms, the body or both, may comprise individually controlled sections, e.g., similar to the sections of FIG. 7, to permit temperature control of various sections of the heating device 910. In use of the heating device 910, the heating device 910 can be inserted toward the end 924 of the column 920 in a similar manner as described in connection with FIGS. 1A-6B. The exact speed at which the heating device 910 is inserted may vary depending on the analyte components on the column 920. The heating device 910 can be used to provide a substantially linear thermal gradient or can be used to provide a non-linear gradient. Once the heating device 910 is inserted to a desired final position, the heating device 910 may be moved back to an initial position prior to a subsequent sample injection into the device. In some embodiments, the temperature provided by the arms 912, 914 and 916 may be about the same for a selected radial plane of the heating device 910. If desired however, any one of the arms 912, 914 or body 916 may have a different temperature than other portions of the heating device 910. For example, the arms 912, 914 may be present at a first temperature and the body 916 may be present at a second temperature different from the first temperature. If desired, the arms 912, 914 may be electrically coupled to a first power source and the body 916 may be electrically coupled to a second power source. In alternative configurations, the arms 912, 914 and body 916 are electrically coupled to a common power source. While the heating device 910 is described as being moved, the column 920 could instead be moved while the heating device 910 remains stationary. Alternatively, both the column 920 and the heating device 910 can be moved if desired.

Figure 10:
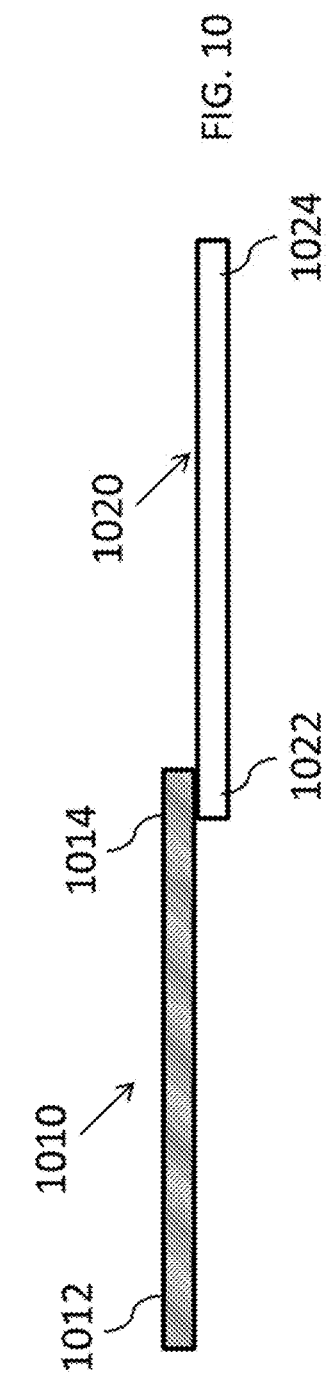
FIG. 10 is an illustration of a heating device configured for use with a wafer column, in accordance with certain examples.

In certain embodiments, the columns used with the heating device described herein may not necessarily be coiled. For example, a cartridge column, wafer column, etc. that is substantially planar may be used with a heating device. Referring to FIG. 10, a wafer column 1020 is shown as a substantially planar device. The column 1020 is thermally coupled to a heating device 1010 which can take the form of a plate. The column comprises an inlet end 1022, which can be fluidically coupled to an injector or other sample introduction device (not shown), and an outlet end 1024, which can be fluidically coupled to a detector (not shown) or other device. The heating device 1010 comprises a first end 1012 and a second end 1014. In use of the heating device 1010, the heating device can be moved from the end 1022 of the column 1020 to the end 1024 of the column 1020. The heating device 1010 may physically contact the top surface of the wafer column 1020 or may ride, for example, along a groove or track in the housing of the column 1020. The exact type of gradient provided by the heating device 1010 may be linear, substantially linear or non-linear. While not shown, air can be provided from the end 1024 of the column toward the end 1014 of the heating device 1010 to provide a thermal gradient from the end 1012 to the end 1014. Once the end 1014 of the heating device 1010 is at or near the end 1024 of the column 1020, the heating device 1010 can be moved back to an initial position prior to injection of an additional sample into the wafer column 1020. Alternatively, the heating device 1010 may remain stationary and the column 1020 may instead be moved. If desired, both the heating device 1010 and the column 1020 can be moved.

In some configurations where a wafer column is used, it may be desirable to configure the heating device with a plate that can provide thermal coupling to each side of the wafer column. Referring to FIG. 11, a wafer column 1120 is shown as a substantially planar device. The column 1120 is thermally coupled to a heating device that comprises a first plate 1000 and a second plate 1010. The column 1120 comprises an inlet end 1122, which can be fluidically coupled to an injector or other sample introduction device (not shown), and an outlet end 1124, which can be fluidically coupled to a detector (not shown) or other device. The plate 1100 comprises a first end 1102 and a second end 1104, and the plate 1110 comprises first end 1112 and a second end 1114. In use of the heating device, the plates 1100, 1110 can be moved from the end 1122 of the column 1120 to the end 1124 of the column 1120. Each of the plates 1100, 1110 may physically contact a surface of the wafer column 1120 or may ride, for example, along a groove or track on the housing of the column 1120. The exact type of gradient provided by the plates 1000, 1110 may be linear, substantially linear or non-linear. While not shown, air can be provided from the end 1124 of the column toward the ends 1104, 1114 to provide a thermal gradient between the ends of the plates 1100, 1110. Once the ends 1004, 1114 of the plates are at or near the end 1124 of the column 1120, the plates 1100, 1110 can be moved back to an initial position prior to injection of an additional sample into the wafer column 1120. The plates 1100, 1110 typically are at the same temperature for a selected radial plane, but if desired, the plates 1100, 1110 may provide different temperatures or different thermal gradients to the column 1120. In an alternative configuration, the plates 1100, 1110 may remain stationary and the column 1120 may instead be moved. In other instances, both the plates 1100, 1110 and the column 1120 can be moved.

In certain configurations, the body of the heating device may comprise holes or apertures in certain portions to provide a thermal gradient from one end of the heating device to the other. Referring to FIG. 12, a heating device 1200 comprises a body with a first end 1210 and a second end 1220. The body may be generally solid at the end 1210 and may comprise apertures 1230 and 1232 at the end 1220 to permit air to flow into the end 1220 and cool the end 1220 to a temperature below the end 1210. While the apertures 1230 and 1232 are shown as being positioned along the longitudinal axis L of the heating device 1200, the apertures may instead be positioned radially in the end 1220 of the device 1200 to permit some air to flow into that end of the heating device 1200 in the longitudinal direction of the axis L. Further, the apertures need not be circular but instead may take other shapes and sizes including rectangular, square, elliptical, etc. In addition, different apertures need not have the same size or shape. In some instances, the heating device may comprise removable plugs that can be inserted into the apertures to close up the space. For example, the plugs can be removed when a larger thermal gradient is desired or be present when a lower thermal gradient is desired. The plugs may fit through a friction fit or through other means as desired. In some instances, the plugs may comprise the same material as the rest of the body of the heating device such that the thermal properties of the plug are about the same as the rest of the body of the heating device. In certain examples, the heating device may comprise a sliding cylinder portion that can be moved relative to the other portion of the heating device to permit the apertures to be open or to be closed depending on the position of the sliding cylinder. Alternatively, the cylinder portion can be rotated to either open or close the apertures of the heating device to at least some degree as desired.

In certain configurations, the heating device may comprise a solid body but different portions of the heating device may comprise different materials. For example, materials that provide a different temperature for a selected applied current may be present to tune the thermal gradient provided by the heating device even further. The different materials can be brazed to each other, welded to each other, soldered to each other or otherwise coupled to each other in some manner, e.g., through a material such as a high temperature adhesive or ceramic. If desired, more than two different materials can be present to provide for further temperature control of the heating device. In some configurations, a coating of a particular material may be present on certain areas of the heating device and absent from other areas of the heating device to provide for further temperature control of the heating device. In other instances, a coating may be present along the surfaces of the heating device, but the overall thickness of the coating may be different in different areas to permit further control of the temperature.

In certain examples, the heating device may be configured to function with an accessory device that remains coupled to the column. For example, a chromatography column can be coiled around a hollow cylinder comprising a central aperture that can receive the heating device. The hollow cylinder can transfer heat from the heating device through the hollow cylinder and to the coiled column. The use of a hollow cylinder may be desirable, for example, where the column is delicate or where direct contact of the moving heating device to the column is not desired. The accessory device need not be a hollow cylinder but may instead be a series of tracks coupled to the column, a cage, a barrel or other forms which can couple to a chromatography column and provide for thermal transfer from the heating device to the chromatography column.

In certain configurations, the heating devices described herein may be configured for use with non-coiled columns. For example, the heating device may be configured as a cylinder or cartridge with a central opening that can receive a non-coiled chromatography column. In some instances, the central opening may be sized and arranged so that it is slightly larger than the dimensions of the non-coiled chromatography column. In use, the heating device is moved so that the column enters into the central opening of the heating device, and a thermal gradient is provided to that portion of the column positioned within the central opening of the heating device. The heating device can be moved from the inlet of the column toward the outlet to provide a thermal gradient along the length of the column. Alternatively, the column can be moved into the heating device, or both the column and the heating device can be moved.

In certain embodiments, the heating devices described herein may be used with a non-conductive column. For example, the columns may be considered insulators or otherwise are substantially electrically non-conductive. This configuration prevents transfer of the current applied to the heating device to the column itself when/if the heating device contacts the column. Without wishing to be bound by any particular theory, charging of the column may induce local thermal gradients within the column itself as those portions of the column can heat up, which can act to reduce the overall precision and accuracy of chromatographic runs. Where a conductive column housing is present, an insulating sleeve or other electrically non-conductive member may be coupled to the housing to prevent current transfer from the heating device to the column. If desired, however, a conductive column can be used. For example, a conductive column can be separated from a heating device through one or more insulator tracks designed for the heating device to ride along.

In certain configurations, the heating device described herein can function as, or similar to, a resistive heater or a thermoelectric heater. For example, a current can be applied to a conductive portion of a resistive heating element in the heating device to provide the heat. In other instances, a solid state active heat pump, e.g., a thermoelectric heater, may be present within the heating device and functions to provide a temperature difference based on current flow through the device. In some instances, the entire body of the heating device may comprise or function as a resistive heating element or a thermoelectric heater, whereas in other instances one or more resistive heating elements of thermoelectric heaters can be present and used to transfer heat to other portions of the heating device. In operation, a substantially constant current may be applied to the heating device during the separation, and a thermal gradient may be provided by cooling one area of the heating device and/or permitting increased air flow to one area of the heating device. If desired, the applied current may be altered during the chromatographic separation to alter the thermal gradient. Where the heating device is configured with one or more sections, different types or a different number of heating devices may be present in different sections to provide temperature differences in different sections of the heating device.

In some instances, the heating device may be produced using conductive or semi-conductive materials that can provide the desired heating and/or temperature difference between different areas of the heating device. Suitable materials include but are not limited to, nickel, chromium and alloys and materials including nickel and chromium, e.g., Nichrom, tungsten, silicon or other materials or combinations of metals or materials. In some instances, the heating device has a thermal mass substantially larger than the thermal mass of the column. Movement of the high thermal mass heating device adjacent to a portion of the low thermal mass column (or movement of the column toward the heating device) can cause the temperature of that portion of the column to quickly become about the same temperature as that area of the heating device. The high thermal mass of the heating device can reduce thermal fluctuations and provide rapid temperature adjustment of different areas of the column. In some instances, the heating device has sufficient thermal mass such that the temperature of an adjacent column portion rises to about the same temperature as the heating device within less than about 1 second.

Figure 13:
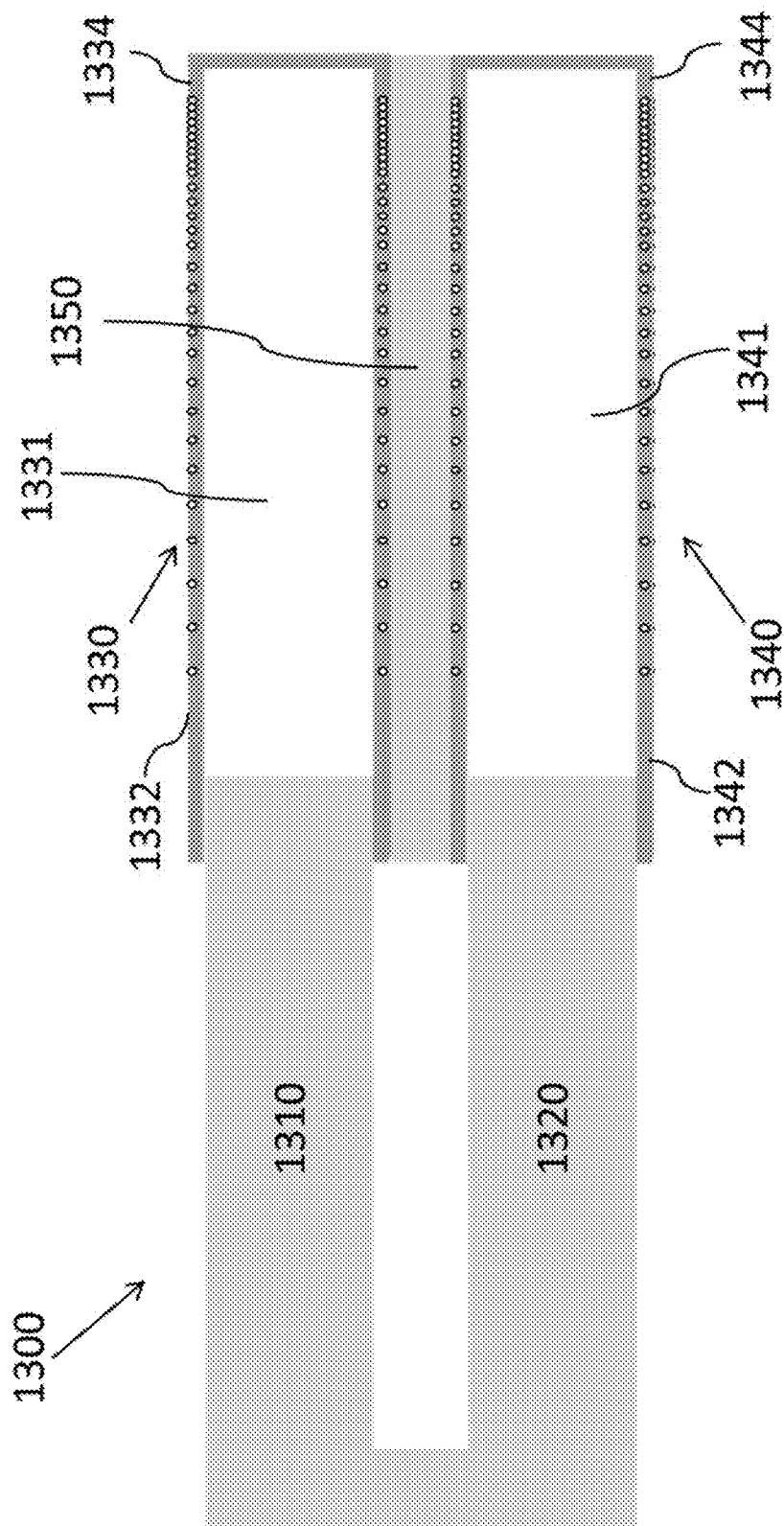
FIG. 13 is an illustration of a heating device that can be used simultaneously with two coiled columns, in accordance with certain examples.
Figure 14:
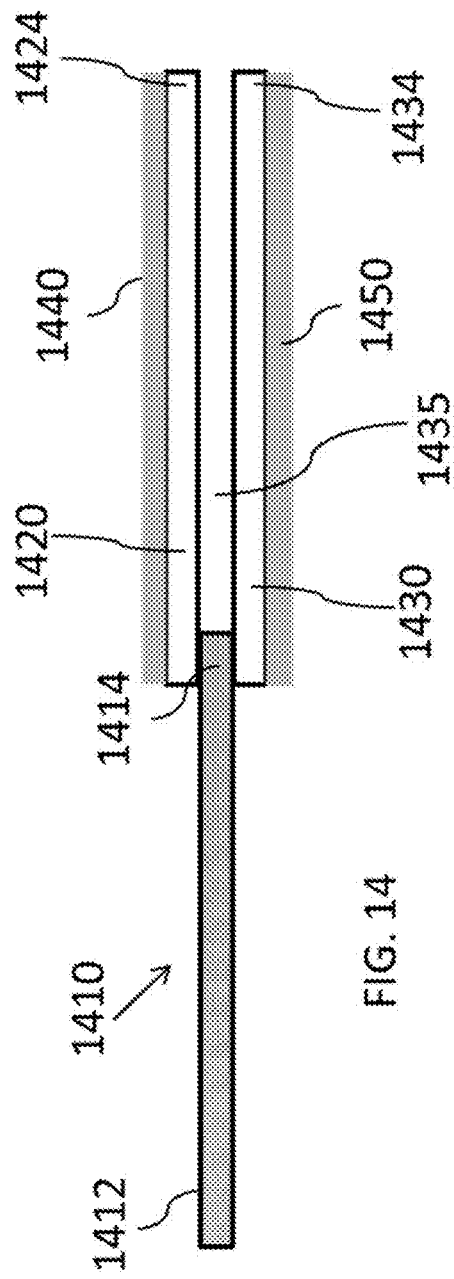
FIG. 14 is an illustration of a heating device that can be used simultaneously with two wafer columns, in accordance with certain examples.

In certain configurations, the heating devices described herein may be used with more than a single column. For example, a single heating device can be configured for use with two or more coiled columns, two or more wafer columns or column bundles, e.g., capillary column bundles, etc. Two illustrations are shown in FIGS. 13 and 14. Referring to FIG. 13, a heating device 1300 is shown that can include two members 1310, 1320 and that can be moved into inner space formed by each of columns 1330, 1340. An insulating member 1350 may be present between the two columns 1330, 1340 to prevent heat transfer away from each of the columns 1330, 1340 to any open space between the columns 1330, 1340. While the coils of each of the columns 1330, 1340 are shown as being spaced closer together toward ends 1334, 1344, the spacing of the column coils can be about the same from the end 1332 to the end 1334 and from the end 1342 to the end 1344. In use of the heating device 1300 and the columns 1330, 1340, the heating device 1300 can be inserted into the open space 1331, 1341 formed by coiling of the columns 1330, 1340, respectively. The speed of insertion of the heating device 1300 can be controlled by a motor (not shown) or other device coupled to the heating device 1300. In the configuration shown in FIG. 13, the positions of the members 1310, 1320 are fixed relative to each other and are generally in the same plane with each other. If desired, however, one of the members 1310, 1320 can be offset or can be individual controlled so movement of the members 1310, 1320 occurs at a different speed or rate. Similarly, the members 1310, 1320 need not be sized or configured the same as each other and may take different lengths, include different materials or have different shapes or overall construction. While not shown, cooling air can be introduced from the ends 1334, 1344 toward the ends 1332, 1342 of the columns 1330, 1340 to assist the heating device 1300 in providing a thermal gradient to the columns 1330, 1340. While the heating devices 1310, 1320 of FIG. 13 are described as being moved, the columns 1330, 1340 could instead be moved or both the heating devices 1310, 1320 and the columns 1330, 1340 can be moved.

Referring now to FIG. 14, a heating device configured for use with two wafer columns is shown. The heating device 1410 is configured as a single plate comprising a first end 1412 and a second end 1414. Two wafer columns 1420 and 1430 are shown positioned adjacent to the end 1414 of the heating device 1410. Optional insulating members 1440, 1450 can be present to reduce heat transfer away from the wafer columns 1420, 1430. In use of the heating device 1410, the heating device 1410 can be inserted into the space 1435 between the wafer columns 1420, 1430 until it reaches an exit end 1424, 1434 of the wafer columns 1420, 1430 to provide a thermal gradient to different portions of the wafer columns 1420, 1430 during movement of the heating device 1410. While not shown, cooling air can be introduced from the ends 1424, 1434 toward the heating device 1410 to assist the heating device 1410 in providing a thermal gradient to the wafer columns 1420, 1430. While a heating device configured as a single plate 1410 is shown in FIG. 14, where two or more wafer columns are present, the heating device may comprise more than a single plate or be configured as a heating device that takes forms other than a plate. In addition, the columns 1420, 1430 may be moved instead of moving the heating device 1410, or both the heating device 1410 and the columns 1420, 1430 can be moved.

Figure 15:
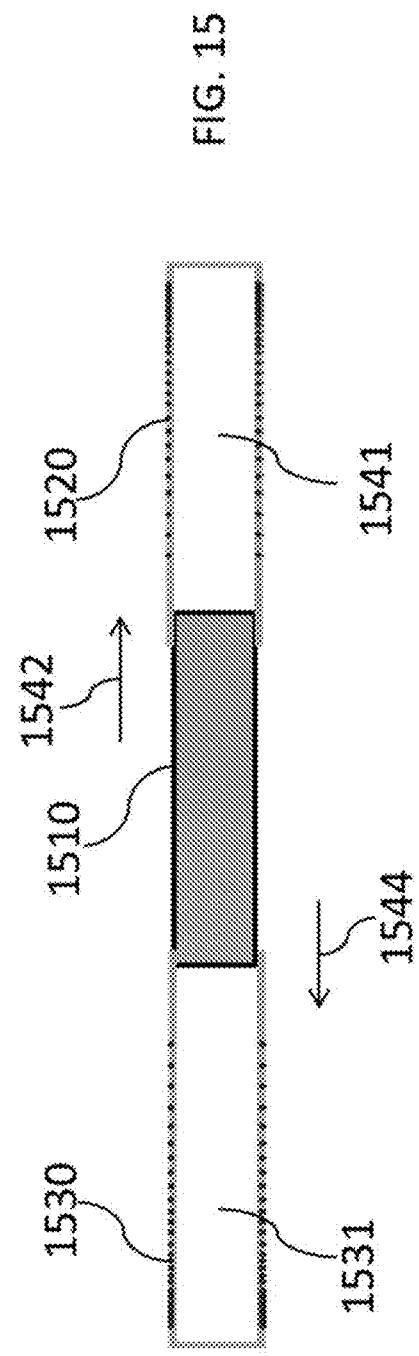
FIG. 15 is another illustration of a heating device that can be used with two coiled columns, in accordance with certain embodiments.

In certain embodiments, a column bundle which comprises a plurality of coiled column may be used with a heating device. The heating device can be configured to contact or be adjacent to inner surfaces of column coils or outer surfaces of column coils or combinations thereof to permit thermal transfer from the heating device to each column in the bundle. In some instances, column bundles can be arranged in antiparallel configurations such that movement of the heating device in one direction thermally couples the heating device to a first column, and movement of the heating device in an anti-parallel direction thermally couples the heating device to a second column. One illustration is shown in FIG. 15. A heating device 1510 is shown positioned between a first column 1520 and a second column 1530. When the heating device 1510 is moved in the direction of arrow 1542 into the inner space 1541 formed from the coiled column 1520, the heating device 1510 provides a thermal gradient along the column 1520. If desired, air, for example, can be blown from the end of the column 1520 toward the heating device 1510 to assist the heating device 1510 in providing the thermal gradient to the column 1520. The heating device 1510 may then be moved antiparallel in the direction of arrow 1544 to thermally couple the heating device 1510 to the column 1530. If desired, air can be blown from the end of the column 1530 toward the heating device 1510 to assist the heating device 1510 in providing the thermal gradient to the column 1530. The heating device can then be moved back to its initial or starting position. In some instances, the two columns 1520, 1530 can each receive the same sample from an introduction device, whereas in other examples the columns 1520, 1530 may receive different samples, e.g., from different injectors or sample introduction devices. While the heating device 1510 is shown as being about the same length as each of the spaces 1531, 1541, the heating device 1510 can be sized differently, e.g., can be T-shaped such that the upper portion of the T-shaped heating device can be thermally coupled to one or more columns by movement.

In certain configurations, movement of the various heating devices and columns described herein can be provided using a motor coupled to the heating device or to the column or both. Where both the column and the heating device is moved, a common motor or two separate motors may be present. Numerous different types of motors are possible including, but not limited to, electric powered motors, pneumatic motors, hydraulic motors and other suitable motors. In some instances, the motor may be a DC electric motor such as a stepper motor that can be coupled to the heating device (or the column) through a shaft or other means. The electric motor can be used to adjust the position of the heating device relative to the column or the position of the column relative to the heating device. For example, the motor may be incrementally stepped to insert the heating device further into the space formed by coiling of the column. Referring to FIG. 16A, a motor 1620 coupled to a heating device 1630 through a shaft 1625 is shown. The heating device 1630 is shown as being configured to insert into open space 1642 formed from a coiled column 1640. In use of the motor 1620, the motor 1620 can be configured to move the heating device 1630 into the space 1642 at a desired or controlled rate. For example, the rate at which the motor 1620 moves the heating device 1630 can control the temperature along the length of the column 1640. While not shown, a fan or other device can provide air from the end of the column 1640 to assist in providing a thermal gradient from the heating device 1630. Alternatively, a heat sink, cooling rod or Peltier cooler can be coupled to one end of the heating device 1630 to provide a lower temperature at that end. If desired, the motor 1620 could instead be coupled to the column 1640 to permit movement of the column 1640 toward the heating device 1630. Alternatively, a second motor may be present and coupled to the column 1640 to permit movement of both the column 1640 and the heating device 1630.

In certain configurations, the speed of the movement may be controlled, for example, by a processor electrically coupled to the motor. A simplified block diagram is shown in FIG. 16B. A processor 1650 is electrically coupled to a motor 1620 which is coupled to a heating device 1630, through a shaft 1625, that is shown partially inserted into a space 1642 formed by coiling a column 1640. The processor 1610 can control the motor 1620 and in turn control the speed at which the heating device 1630 is inserted into the space 1642. While not shown, the processor 1610 can also be electrically coupled to a power source, which itself can be coupled to the heating device 1630. The processor 1610 may control the level of current provided from the power source to the heating device 1630 to control the temperature of the heating device 1630. Where a fan (not shown) is present to assist in providing the thermal gradient from the heating device 1630 to the column 1640, the fan can be electrically coupled to the processor 1610 to control the fan speed. The processor 1610 can also be used to control the chromatographic separation if desired and/or may be used by the detector (not shown) and/or a display to output the results of a chromatographic run.

In certain configurations, the motor 1620 may be a brushed or brushless electric motor configured to incrementally move the heating device 1630 into the space 1642. If desired, one or more gears, transmissions, etc. can be present to further assist in movement of the heating device 1630 in a desired direction and at a desired speed. Similar devices can be used where a motor is coupled to a column. If desired, more than a single electric motor can be present to further control movement of the heating device (or column) in a desired direction and/or at a desired speed. In some instances, the exact configuration of the electric motor may depend on the particular power source used. As noted herein, DC power sources may be desirable in portable applications where the chromatography systems are used remotely from an available AC power source. AC power sources can also be used in addition to, or in place, of, a DC power source. Illustrative motors that can be used include, but are not limited to, a brushed DC motor, a brushless DC motor, an AC induction motor, a permanent magnet synchronous motor, a stepper motor and a switched reluctance motor. The motor may be a single phase motor or a multi-phase motor and can be controlled in many different manners including voltage modulation such as, for example, pulse width modulation or other means.

In other configurations, the motor 1620 can be configured as a pneumatic motor that can use air pressure to move the shaft 1625 and the heating device 1630 in a desired direction. The pneumatic motor may comprise a compressor or use air pressure from the chromatography system to convert the air pressure into mechanical movement of the heating device 1630. Where a pneumatic motor is used, the pneumatic motor may comprise, or be configured as, a diaphragm or a piston actuator that can move the heating device 1630 into and out of the space 1642. For example, the pneumatic motor can be configured as a spring piston coupled to a solenoid valve which can be actuated open by the processor 1610 to apply pressure to the piston and force the piston in a certain direction and cause movement of the heating device 1630. The valve can be closed and the pressure released to permit the spring to return to its resting position and retract the piston and heating device 1630. Pneumatic motors may be desirable to use, for example, in volatile environments where sparks should be avoided or where available DC or AC power is limited. If desired, a pneumatic motor can instead be coupled to a column to control movement of the column.

In certain embodiments, the motor may be configured as a hydraulic motor that can be coupled to the heating device 1630, for example, through one of more gears to permit movement of the heating device 1630 in a desired manner. While not wishing to be bound by any particular theory, the hydraulic motor may convert hydraulic pressure into mechanical movement. The exact configuration of the hydraulic motor may vary and may include, but is not limited to, gear and vane hydraulic motors, gerotor hydraulic motors, axial plunger hydraulic motors, and radial piston hydraulic motors. Where the hydraulic motor is designed to cause angular rotation, one or more gears, differentials or transmissions may be present to convert the angular motion to a linear motion to permit movement of the heating device 1630 in a desired direction. In some instances, it may be desirable to use a first hydraulic motor to move the heating device in a first direction and use a second hydraulic motor to move the heating device back to an initial position. The braking effect provided when the hydraulic motor is not in use can be used to assist in control of the movement of the heating device at a desired speed. If desired, a hydraulic motor can instead be coupled to a column to control movement of the column.

While various embodiments described herein refer to the heating device being moved relative to a stationary column, if desired, the heating device may instead remain stationary and the column can be moved. For example, the column can be coupled to one or more of the motors described herein and moved into the heating device (or alongside of the heating device) at a desired speed to provide a thermal gradient to the moving column from the stationary heating device. Further, if desired both the heating device and the column can be moved to further control the application of the thermal gradient to the column. For example, it may be desirable to use motors having a different number of steps with the heating device and with the column to provide for finer movement of the heating device and the column. A single processor or multiple processors can be used to control the two motors where both the heating device and the column are moved. If desired, a single motor can be used to control movement of both the heating device and the column.

In certain embodiments, the exact power source used with the heating device may depend on the particular configuration of the chromatography system. Where AC power is used, the AC power may be provided from a utility grid, a generator or other AC power sources. Where the chromatography system takes the form of a portable device or system (as described in more detail below), the power source may be a DC power source including, but not limited to, solar cells, batteries or other electrochemical cells, fuel cells, wind turbine generators, crank generators, or DC power provided from a remote power source such as diesel generator, tractor power take off coupled to an alternator or generator, or other fuel powered engines that can generate DC power. The power source may be configured as a hot swappable power source so as the power source is drained an additional power source can be interchanged with it. In some instances, the systems may include two or more different power sources to permit swapping of the power sources without needing to shut down the entire system. For example, the system may be designed to use a first power source until the first power source drains to a certain level and then automatically switch over to a second power source. The first power source may then be swapped out with a charged power source. Once the second power source drains to a certain level, the system can revert to using the charged first power source to permit the user to swap out the drained second power source. Alternatively, the system can include back up power that is used when a primary power source is absent or too low for operation. The primary and/or back up power sources can be on board the device or can be coupled to the device using a wired interconnect or wireless coupling such as through the use of a wireless connection, e.g., an inductive charger or inductive power source.

In certain embodiments, the exact temperature gradient provided from the heating device may vary depending on the species to be analyzed. In some instances, one end of the heating device may provide a temperature of up to about 350 degrees Celsius or up to about 400 degrees Celsius or up to about 450 degrees Celsius or even up to about 500 degrees Celsius. Higher temperatures are also possible if desired. The temperature may decrease linearly at a rate of about 1 degrees Celsius/cm to about 50 degrees Celsius/cm or even greater than 50 degrees Celsius/cm along the length of the heating device from the hot end to the colder end. In other instances, the temperature may decrease in a non-linear fashion with curves, stepped temperatures or plateaus present over a desired distance, e.g., a thermal gradient having a profile that is substantially monotonically non-increasing and has a positive second derivative as described in U.S. Ser. No. 14/488,013 filed on Sep. 16, 2014 can be implemented using the heating device. If desired, one or more temperature sensors, e.g., thermocouples or other temperature measuring devices, can be present at desired areas of the heating device to provide a measure of the temperature at that area. In some configurations, the temperature sensors can be electrically coupled to the processor to permit the processor to control the current level provided to the heating device and alter the temperature as desired.

Figure 17:
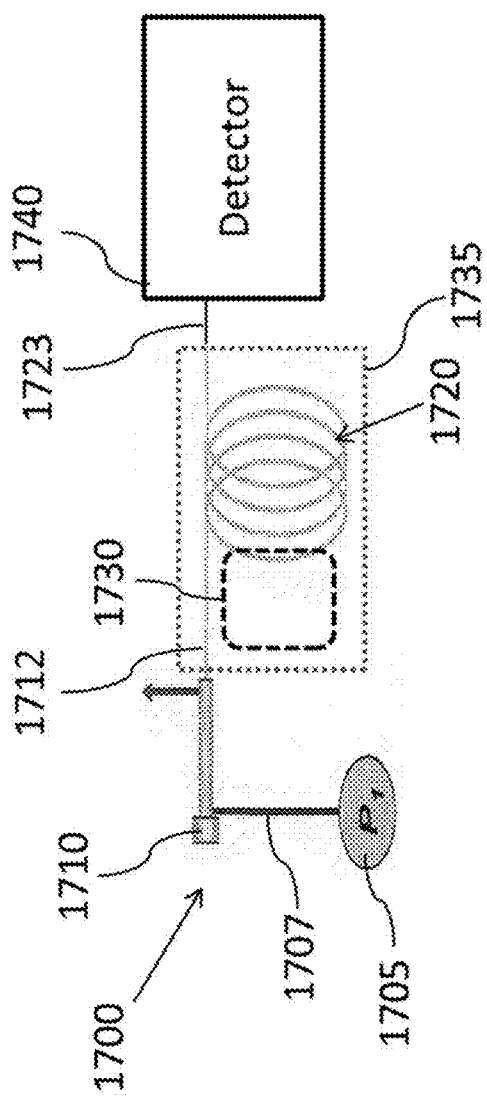
FIG. 17 is an illustration of a gas chromatography system comprising an injector, an oven, a heating device, a column and a detector, in accordance with certain configurations.

In certain embodiments, the heating device described herein may be present in a gas chromatography (GC) system. Referring to FIG. 17, a typical GC system 1700 comprises an injector 1710 fluidically coupled to a column 1720 through a fluid line 1712. The injector is fluidically coupled to a pressure source 1705 that can provide a gas, e.g., a carrier gas, to the injector 1710 through a fluid line 707 and/or to the column 1730 through the fluid line 1712. A heating device 1730 is shown that can be inserted into the open space formed by the column 1720 to provide a thermal gradient to the column 1720. A fan (not shown) can be positioned on the other side of the column 1720 to blow air into the open space formed by the column 1720. The heating device 1730 and column 1720 can be positioned in an oven 1735 configured to maintain the column 1720 at a desired temperature before the heating device 1730 is inserted into the space formed from the coiled column 1720. The injector 1710 may be, for example, a split or splitless injector, or other types of injectors commonly used in GC devices. The column 1720 can be fluidically coupled to a detector 1740 through a fluid line 1723. As noted herein, the column 1720 may take many forms including capillary columns, capillary column bundles, wafer columns, column cartridges or other types of columns. The heating device 1730 may take many forms as described herein. The detector 1740 may also take many forms depending on the type of analyte to be detected. For example, the detector 1740 may be a mass spectrometer, a thermal conductivity detector, a flame ionization detector, a flame photometric detector, a photoionization detector, an infrared detector, a catalytic combustion detector, a discharge ionization detector, an electron capture detector, a thermionic detector, a nitrogen-phosphorous detector or other detector commonly used with GC devices.

Figure 18:
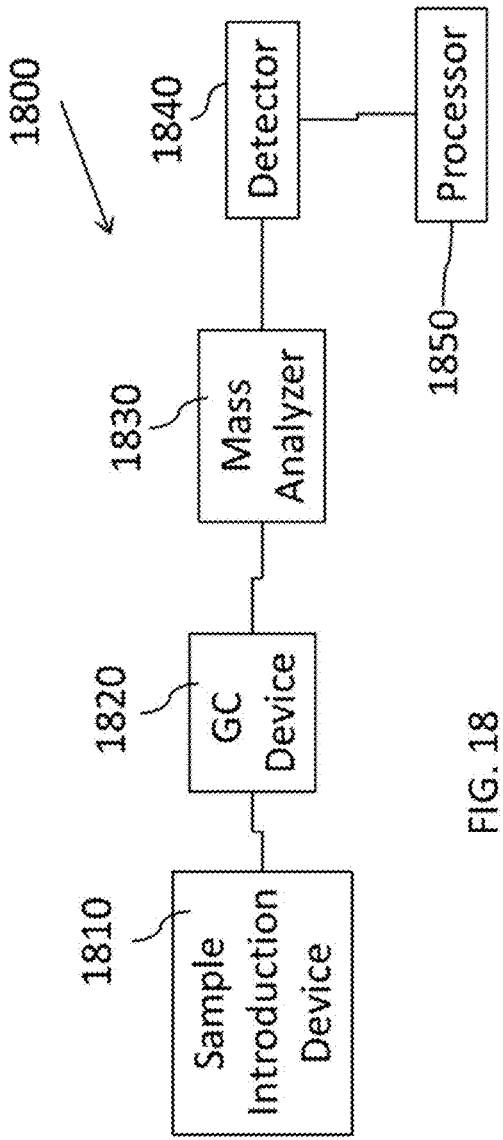
FIG. 18 is a block diagram showing a system comprising a gas chromatography device coupled to a mass spectrometer, in accordance with certain examples.

In certain configurations, the GC devices comprising a heating device may be hyphenated with one or more other devices. For example, tandem GC-GC device, GC-mass spectrometer (MS) devices or other tandem devices where one of the device comprises a heating device as described herein may be used. In certain embodiments, the GC devices described herein may be used with a mass spectrometer. A block diagram of one system is shown in FIG. 18. The GC-MS device 1800 comprises a sample introduction device 1810, a GC device 1820 comprising a heating device, a mass analyzer 1830, a detector 1840, a processing device 1850 and an optional display (not shown). The sample introduction device 1810, the GC device 1820, the mass analyzer 1830 and the detector 1840 may be operated at reduced pressures using one or more vacuum pumps such as roughing pumps and/or turbomolecular pumps. In certain examples, however, only the mass analyzer 1830 and the detector 1840 may be operated at reduced pressures. The sample introduction device 1810 may include an inlet system configured to provide sample to the GC device 1820. The inlet system may include one or more batch inlets, direct probe inlets and/or chromatographic inlets and/or injectors. For example, the sample introduction device 1810 may be an injector, a nebulizer or other suitable devices that may deliver solid, liquid or gaseous samples to the GC device 1820. The GC device 1820 typically comprises a column and heating device as noted in connection with FIG. 17. The mass analyzer 1830 may take numerous forms depending generally on the sample nature, desired resolution, etc. and exemplary mass analyzers are discussed further below. The detector 1840 may be any suitable detection device that may be used with existing mass spectrometers, e.g., electron multipliers, Faraday cups, coated photographic plates, scintillation detectors, etc., and other suitable devices that will be selected by the person of ordinary skill in the art, given the benefit of this disclosure. The processing device 1850 typically includes a microprocessor and/or computer and suitable software for analysis of samples introduced into GC-MS device 1800. One or more databases may be accessed by the processing device 1850 for determination of the chemical identity of species introduced into MS device 1800. Other suitable additional devices known in the art may also be used with the MS device 1800 including, but not limited to, autosamplers, such as AS-90plus and AS-93plus autosamplers commercially available from PerkinElmer Health Sciences, Inc.

In certain embodiments, the mass analyzer of MS device 1800 may take numerous forms depending on the desired resolution and the nature of the introduced sample. In certain examples, the mass analyzer can be a scanning mass analyzer, a magnetic sector analyzer (e.g., for use in single and double-focusing MS devices), a quadrupole mass analyzer, an ion trap analyzer (e.g., cyclotrons, quadrupole ions traps, a miniaturized toroidal ion trap), time-of-flight analyzers (e.g., matrix-assisted laser desorbed ionization time of flight analyzers), and other suitable mass analyzers that may separate species with different mass-to-charge ratios. The GC devices disclosed herein may be used with any one or more of the mass analyzers listed above and other suitable mass analyzers.

In certain other examples, the chromatography devices disclosed here may be used with existing ionization methods used in mass spectroscopy. For example, electron impact sources in combination with a GC device may be used. In other examples, chemical ionization sources in combination with a GC device may be used. In yet other examples, field ionization sources in combination with a GC device may be provided. In still other examples, the GC devices may be used with desorption sources such as, for example, those sources configured for fast atom bombardment, field desorption, laser desorption, plasma desorption, thermal desorption, electrohydrodynamic ionization/desorption, etc. In yet other examples, the GC devices may be configured for use with thermospray ionization sources, electrospray ionization sources or other ionization sources and devices commonly used in mass spectroscopy. It will be within the ability of the person of ordinary skill in the art, given the benefit of this disclosure, to design suitable devices for ionization that also use a chromatography device or GC device as described herein.

In certain examples, the chromatography devices described herein can be used in portable devices. For example, a small portable gas cylinder or gas cartridge similar to the size of a small propane tank, e.g., a 1 liter tank, a 1-gallon tank or a 5-gallon tank, can be filled with helium or other suitable carrier gas or air can be used as a carrier gas. The gas cylinder can be fluidically coupled to the GC device to permit chromatographic separations and/or analyses. Illustrative portable device applications include, but are not limited to, soil analysis, hydrocarbon fluid analysis, air space analysis or other environment analysis, pharmaceutical analysis, e.g., ADME analyses, food science analysis, perfume analysis, essential oil analysis, veterinary assays or other chemical tests commonly performed in non-laboratory settings.

In some examples, the GC device may be present on a mobile vehicle such as a military vehicle, an aircraft, a satellite, a spaceship or shuttle, an unmanned aerial vehicle, a rocket or missile or other vehicles commonly used in the military and/or in aerospace settings. The vehicle can be propelled, for example, using an engine or through combustion or burning of liquid or gas fuels or may be powered using an electric engine, hybrid engine or a fuel cell. Alternatively, the GC device may be present on devices commonly used by the national oceanic and atmospheric administration including, for example, weather balloons, hurricane aircraft, portable weather devices, ocean buoys or other devices which can transmit information about the atmosphere.

Figure 19:
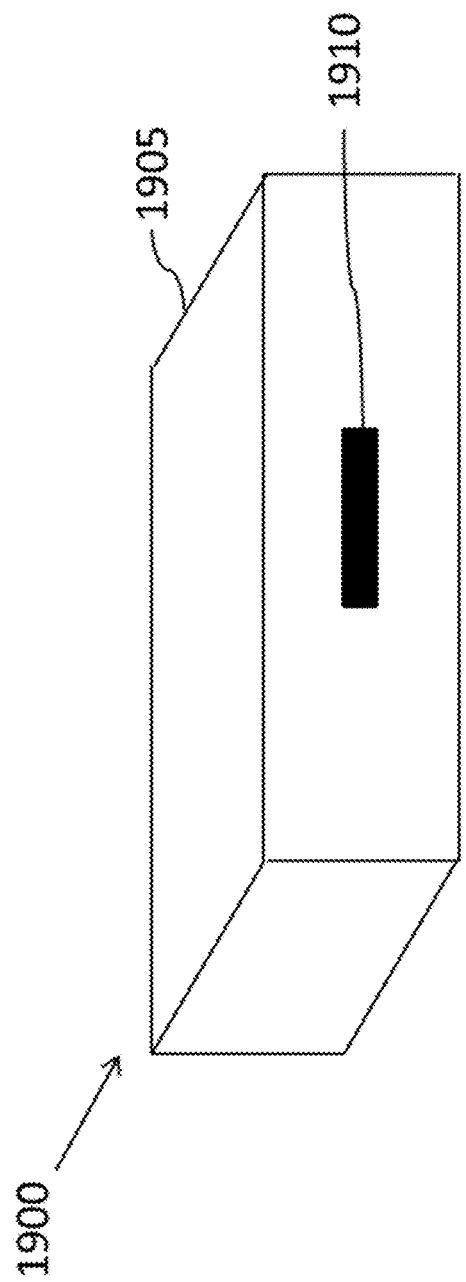
FIG. 19 is an illustration of a portable gas chromatography device, in accordance with certain embodiments.

In yet other configurations, the GC device may be configured similar to a briefcase that can be transported by a human. Referring to FIG. 19, an illustration of a portable GC device is shown. The GC device 1900 comprises a housing 1905 comprising a handle 1910 to assist in carrying of the device 1900. If desired, a carrying strap, wheels or other devices may be present in addition to the handle 1910 or in place of the handle 1910. While the exact dimensions of the device 1900 may vary, illustrative dimensions are about 25-35 cm wide by about 35-45 cm long by about 15-25 cm thick. The exact weight of the device may vary depending on the components present, but illustrative weights include, but are not limited to, about 7.5 kg to about 30 kg, more particularly about 8 kg to about 20 kg or about 10 kg to about 15 kg. While not shown, a cover may be present to prevent damage to a display screen or other device present on a top surface of the housing 1905. Where the device is designed to provide GC-MS analyses, the device 1900 may comprise one or more turbo molecular pumps and/or one or more roughing pumps. The exact type of power source present in the device 1900 may vary from batteries, fuel cells, solar cells or other power sources described herein. In some instances, the power source may be selected to permit about 20-50 analyses until the power source needs to be replaced or recharged. A carrier gas can be coupled to the device 1900 or the device 1900 may comprise an onboard carrier gas or carrier gas cylinder or carrier gas cartridge (which can be replaced or recharged as desired). In some instances, enough carrier gas may be present to permit about 130-170 analyses prior to needing to replace or recharge the carrier gas. The exact carrier gas used can vary and illustrative carrier gases include, but are not limited to, hydrogen, helium, air, nitrogen, argon or other gases. The device 1900 may comprise a sample introduction device such as an injector to permit a user to inject a sample using a syringe. Both liquid and gas samples can be injected as desired. The device 1900 may comprise a processor, a keypad or other components to facilitate use of the device 1900. In some instances, the device 1900 may be configured with a miniaturized toroidal ion trap or other MS devices. The device 1900 may further include a chromatography column, an oven and a detector as noted in connection with FIG. 17.

In some instances, it may be desirable to use two separate heating devices. For example, the heating devices can be held at different temperatures so there is a thermal gradient between the two heating devices. In some instances, one heating device is thermally coupled to a column and then moved away from the column as the second heating device becomes thermally coupled to the column and is moved toward the column. In some examples, the first heating device can be thermally coupled to a column to permit equilibration of the column at substantially the same temperature as the first heating device. The first heating device may then be translated so it is moved completely away from the column prior to insertion of the second heating device into the column. The second heating device can then be inserted into the column to provide a thermal gradient as the second heating device is inserted.

Figure 20:
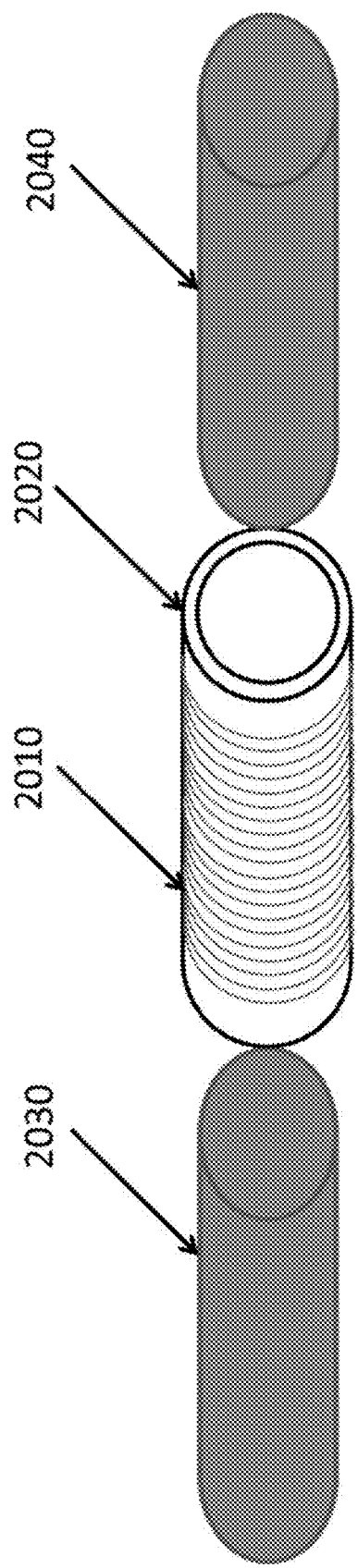
FIG. 20 is an illustration of a system comprising first and second heating devices, in accordance with certain configurations.
Figure 21A:
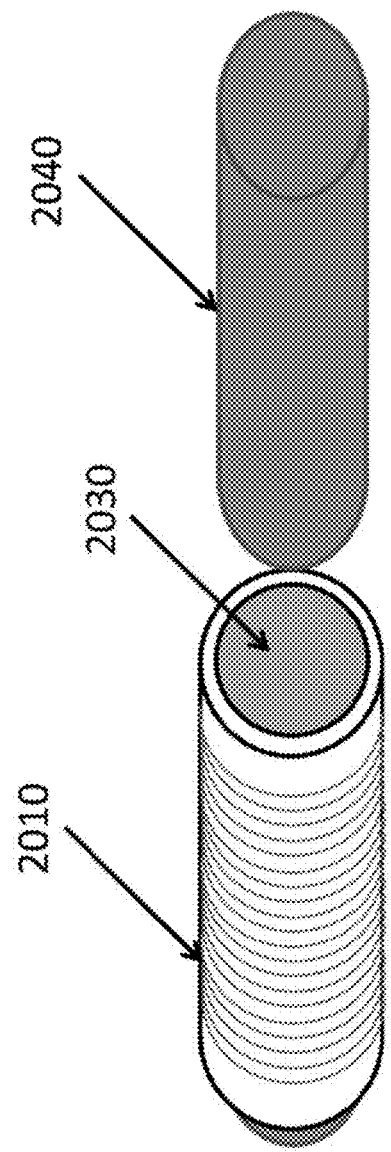
FIG. 21A is an illustration showing insertion of a first heating device into an interior portion of a column, in accordance with certain examples.
Figure 21B:
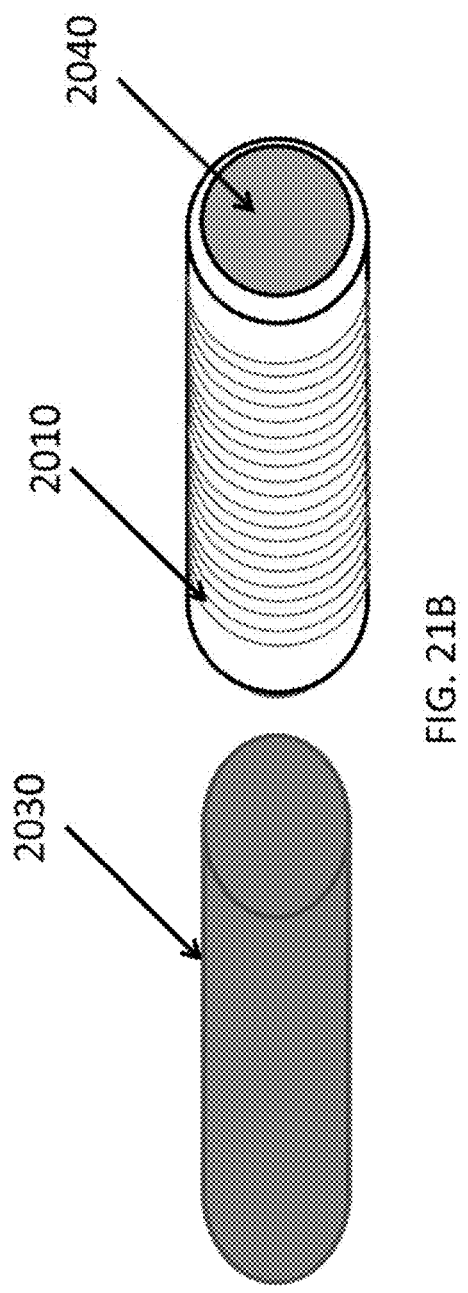
FIG. 21B is an illustration showing insertion of a second heating device into an interior portion of a column, in accordance with certain examples.

Referring to FIG. 20, one illustration of a system comprising two heating devices is shown. The system comprises a column 2010 wound around a substrate 2020. The substrate 2020, e.g., a glass tube or other device, is sized and arranged to receive each of heating devices 2030, 2040. One of the heating devices 2030, 2040 can be cooled to provide a first temperature, and the other of the heating devices 2030, 2040 can be heated to provide a second temperature higher than the first temperature. Each of the heating devices 2030, 2040 can be configured similar to any of the other heating devices described herein and may be configured to surround an outer surface of the column 2010 or both an inner surface of the column 2010 and outer surface of the column 2010. In use of the two heating devices 2030, the heating device at the lower temperature can first be thermally coupled to the column 2010 as shown in FIG. 21A. The device 2030 can then be removed from the interior surface of the column 2010, and the device 2040 can be inserted longitudinally into the column 2010 to provide a thermal gradient. The exact temperature differential of the heating devices 2030, 2040 may vary and illustration temperature differences are about 150 deg. Celsius, 200 deg. Celsius, 250 deg. Celsius or more. In some examples, the heating device 2030 can be held at about 50-60 deg. Celsius, and the heating device 2040 can be held at about 290-300 deg. Celsius. One or more of the heating devices 2030, 2040 may be thermally coupled to a fan to permit alteration of the temperature of that particular heating device. The insertion/removal rates of the heating devices 2030, 2040 can also vary. For example, the heating devices can be inserted at a rate of about ⅛-½ inch every 10 seconds into the interior of the column 2010. If desired, for example, insertion of the heating devices can be controlled in a smooth manner using a stepper motor or other device.

In certain instances, the heating devices 2030, 2040 can be mechanically coupled to each other so when one of the heating devices 2030, 2040 is inserted into the column 2010, the other one of the heating devices 2030, 2040 moves in generally the same longitudinal direction. The longitudinal spacing between the heating devices 2030, 2040 can be selected so that the heating devices 2030, 2040 are not inserted into the interior of the column 2010 at the same time. The heating devices 2030, 2040 can be sized and arranged so they do not contact the interior surface of the column 2010 but are close enough to transfer heat to the column 2010. To enhance thermal transfer, the glass tube 2020 (FIG. 20) can be omitted entirely if desired so heat is transferred directly to the column 2010.

In some embodiments, the heating devices 2030, 2040 can be configured as rods, plates, segmented rods, separate rods, bundled rods or configured in other manners. In some instances, the heating devices rods may comprise one or more apertures or bores which may optionally comprise an internal fan to assist in heat transfer from the heating devices 2030, 2040 to the column 2010. The exact material used in the heating devices 2030, 2040 can vary and illustrative materials include metals such as aluminum or other solid materials which can retain heat well.

Figure 22:
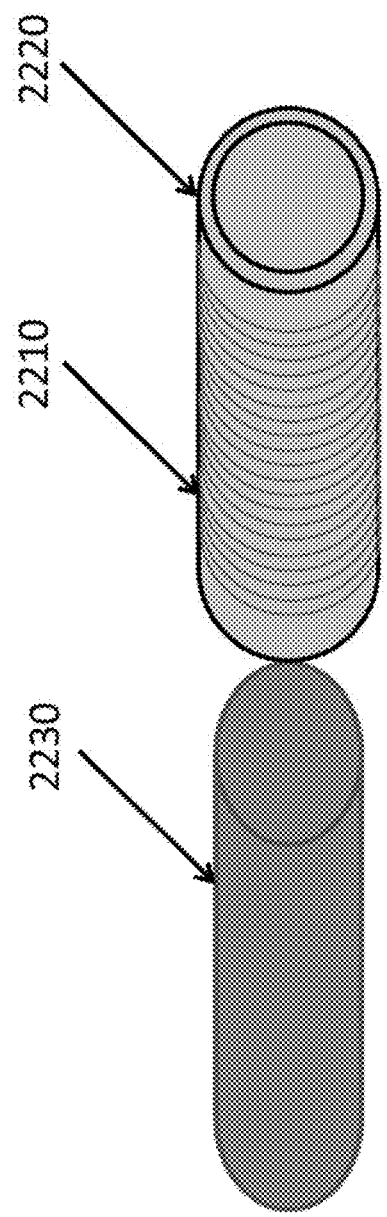
FIG. 22 is an illustration showing two heating devices where one heating device is sued to retain a column, in accordance with certain embodiments.

In some examples, the substrate around which the column is wound may itself act as a heating device. For example and referring to FIG. 22, a system is shown that comprises a column 2210 wound around a first heating device 2220. A second heating device 2230 can be inserted longitudinally into and out of the first heating device 2220. In use of the system of FIG. 22, the heating device 2220 is held at a first temperature to permit the column 2010 to equilibrate at that temperature. The second heating device 2230 can then be inserted into the interior of the first heating device 2230 to transfer heat to the first heating device 2220 and to the column 2210. Insertion of the second heating device 2230 into the first heating device 2220 can provide a thermal gradient which can be used during a chromatographic separation. If desired, the heating device 2230 can be configured to thermally transfer heat to outer surfaces of the column 2210 by sliding over the column 2210 and heating device 2220 rather than being inserted into an interior area of the heating device 2220. While not shown, a third heating device can also be used with the column 2210 and the heating devices 2220, 2230.

In certain embodiments, the GC devices described herein can be used with a device or system comprising a computer or other device that includes a processor. The computer system can be separate or integral to the GC devices. The processor can be used, for example, to control movement of the heating device, movement of the column, oven temperature, control any fans or pumps, control a detector or to otherwise permit use of the GC devices in analyses. The computer system typically includes at least one processor electrically coupled to one or more memory units to receive input data from the GC device. The computer system may be, for example, a general-purpose computer such as those based on Unix, Intel PENTIUM-type processor, Motorola PowerPC, Sun UltraSPARC, Hewlett-Packard PA-RISC processors, or any other type of processor. One or more of any type computer system may be used according to various embodiments of the technology. Further, the system may be connected to a single computer or may be distributed among a plurality of computers attached by a communications network. A general-purpose computer system may be configured, for example, to perform any of the described functions including but not limited to: heating device movement control, temperature control gas flow rate control, detector monitoring, etc. It should be appreciated that other functions, including network communication, can be performed and the technology is not limited to having any particular function or set of functions. Various aspects of the systems and methods may be implemented as specialized software executing in a general-purpose computer system. For example, a protocol configured to control and/or move the heating device to various positions can be implemented. The computer system may include a processor connected to one or more memory devices, such as a disk drive, memory, or other device for storing data. Memory is typically used for storing programs and data during operation of the computer system. Components of the computer system may be coupled by an interconnection device, which may include one or more buses (e.g., between components that are integrated within a same machine) and/or a network (e.g., between components that reside on separate discrete machines). The interconnection device provides for communications (e.g., signals, data, instructions) to be exchanged between components of the system. The computer system typically is electrically coupled to a power source and one or more of the heating device, the column, the detector, the motor, etc. such that electrical signals may be provided to and from the computer and the electrically coupled devices. The computer system may also include one or more input devices, for example, a keyboard, mouse, trackball, microphone, touch screen, manual switch (e.g., override switch) and one or more output devices, for example, a printing device, display screen, speaker. In addition, the computer system may contain one or more interfaces that connect the computer system to a communication network (in addition or as an alternative to the interconnection device). The computer system may also include suitable circuitry to convert signals received from the detector and/or other components of the system. Such circuitry can be present on a printed circuit board or may be present on a separate board or device that is electrically coupled to the printed circuit board through a suitable interface, e.g., a serial ATA interface, ISA interface, PCI interface or the like or through one or more wireless interfaces, e.g., Bluetooth, WiFi, Near Field Communication or other wireless protocols and/or interfaces.

In some instances where portable devices are used, the portable device can be designed to send remote signals to a central office or computer system remote from the portable device. For example, information representative of analyses can be sent remotely to simplify the overall construction of the portable device and/or reduce power requirements of the portable device. Once the information is received remotely, it can be used in determining the components and/or their amounts that were analyzed.

In other instances, the GC device can be configured to function with an accessory device such as a mobile phone, a tablet, a laptop or other device comprising an operating system that is separate from the GC device. In portable applications, it may be desirable to separate the mobile device from the portable device to reduce overall power consumption by the portable device. Signals from the portable device may be sent to the mobile device in a wired or wireless manner to permit viewing of the data/results on the mobile device. In some instances, the mobile device can be coupled to the portable device through a dock or a wired coupler, whereas in other instances, wireless communication between the mobile device and the GC device may be used to transfer information from the portable device to the mobile device. In addition, the mobile device can be pre-programmed or pre-configured to implement certain operations that can automatically load from the mobile device into the GC system. If desired, the mobile device can be designed for use with two or more different systems to permit a single mobile device to implement the same or different operations on the two or more systems. The mobile device may be pre-loaded with the GC routines, standard curves, user instructions, troubleshooting instructions or other information to assist in use of the GC devices. One or more menus can be present on the mobile device to permit the user to select the particular methodology of using the GC device or to troubleshoot operation of the GC device.

In certain embodiments, the storage system of the computer typically includes a computer readable and writeable nonvolatile recording medium in which GC routines can be stored that can be used by a program to be executed by the processor or information stored on or in the medium to be processed by the program. The medium may, for example, be a disk, solid state drive or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in the storage system or in the memory system. The processor generally manipulates the data within the integrated circuit memory and then copies the data to the medium after processing is completed. For example, the processor may receive signals from the detector and can display those signals in a format useful to the end user. A variety of mechanisms are known for managing data movement between the medium and the integrated circuit memory element and the technology is not limited thereto. The technology is also not limited to a particular memory system or storage system. In certain embodiments, the computer system may also include specially-programmed, special-purpose hardware, for example, an application-specific integrated circuit (ASIC) or a field programmable gate array (FPGA). Aspects of the technology may be implemented in software, hardware or firmware, or any combination thereof. Further, such methods, acts, systems, system elements and components thereof may be implemented as part of the computer system described above or as an independent component. Although a computer system is described by way of example as one type of computer system upon which various aspects of the technology may be practiced, it should be appreciated that aspects are not limited to being implemented on the described computer system. Various aspects may be practiced on one or more computers having a different architecture or components. The computer system may be a general-purpose computer system that is programmable using a high-level computer programming language. The computer system may be also implemented using specially programmed, special purpose hardware. In the computer system, the processor is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME), Windows XP, Windows Vista, Windows 7, Windows 8 or Windows 10 operating systems available from the Microsoft Corporation, MAC OS X, e.g., Snow Leopard, Lion, Mountain Lion or other versions available from Apple, the Solaris operating system available from Sun Microsystems, or UNIX or Linux operating systems available from various sources. Many other operating systems may be used, and in certain embodiments a simple set of commands or instructions may function as the operating system.

In certain examples, the processor and operating system may together define a computer platform for which application programs in high-level programming languages may be written. It should be understood that the technology is not limited to a particular computer system platform, processor, operating system, or network. Also, it should be apparent to those skilled in the art, given the benefit of this disclosure, that the present technology is not limited to a specific programming language or computer system. Further, it should be appreciated that other appropriate programming languages and other appropriate computer systems could also be used. In certain examples, the hardware or software can be configured to implement cognitive architecture, neural networks or other suitable implementations. If desired, one or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

In some instances, various embodiments may be programmed using an object-oriented programming language, such as SmallTalk, Basic, Java, C++, Ada, or C# (C-Sharp). Other object-oriented programming languages may also be used. Alternatively, functional, scripting, and/or logical programming languages may be used. Various configurations may be implemented in a non-programmed environment (e.g., documents created in HTML, XML or other format that, when viewed in a window of a browser program, render aspects of a graphical-user interface (GUI) or perform other functions). Certain configurations may be implemented as programmed or non-programmed elements, or any combination thereof.

In using systems comprising a processor, the processor can be designed to provide the various control and functions in a processing time, which is typically orders of magnitude faster than operations that could be performed manually. For example, the processor can be configured to implement various functions in less than 1 millisecond, less than 100 microseconds or even less than 10 microseconds to facilitate rapid control of the GC devices. In some instances, signals provided from the detector to the processor can be displayed or otherwise provided in near real-time to permit a user to view analyses quickly and without the need to manipulate the information manually. The processor can be configured to simultaneously control multiple functions of the GC devices including, for example, motor control, detector operation, gas flows, data display and other operations performed by the GC devices.

In certain embodiments, a kit comprising a heating device configured to thermally couple to a chromatography column at a first position, and instructions for using the heating device with the chromatography column to provide a thermal gradient to the chromatography column during a chromatographic separation by moving the heating device in a longitudinal direction along the chromatography column from the first position to a second position different from the first position can be provided. In some instances, the kit may also include a motor configured to couple to the heating device to move the heating device in the longitudinal direction, e.g., a stepper motor. The kit may be used, for example, to retrofit existing GC devices with the moveable heating devices described herein. The kit may also comprise a processor configured to electrically couple to the motor and control movement of the heating device in the longitudinal direction. If desired, the existing processor of a GC device can be replaced with the processor of the kit or the existing processor can be reprogrammed for use with the heating device. The kit may also include one or more chromatography columns including, but not limited to, a coiled capillary column, a coiled capillary column bundle, a wafer column and a non-coiled capillary column. If desired a DC power source, e.g., at least one of an electrochemical cell, a fuel cell, a solar cell or a wind turbine configured to provide a direct current, can be included in the kit. Additional DC power sources can also be included if desired.

In other configurations, a kit may comprise a heating device configured to thermally couple to a chromatography column at a first position, and instructions for using the heating device with the chromatography column to provide a thermal gradient to the chromatography column during a chromatographic separation by moving the chromatography column in a longitudinal direction along the heating device from the first position to a second position different from the first position. In some configurations, the kit may include a motor, e.g., a stepper motor, configured to couple to the chromatography column to move the chromatography column in the longitudinal direction. The kit may be used, for example, to retrofit existing GC devices with the moveable columns described herein. The kit may also comprise a processor configured to electrically couple to the motor and control movement of the column in the longitudinal direction. If desired, the existing processor of a GC device can be replaced with the processor of the kit or the existing processor can be reprogrammed for use with the column. The exact nature of the moveable column of the kit can vary and illustrative columns include, but are not limited to, a coiled capillary column, a coiled capillary column bundle, a wafer column and a non-coiled capillary column. If desired a DC power source, e.g., at least one of an electrochemical cell, a fuel cell, a solar cell or a wind turbine configured to provide a direct current, can be included in the kit. Additional DC power sources can also be included if desired.

In certain embodiments, a method comprising providing a heating device configured to thermally couple to a chromatography column at an inlet section of the chromatography column in a first position and to thermally couple to the chromatography column at a section downstream from the inlet section in a second position, the heating device configured to move in a longitudinal dimension along the chromatography column from the first position to the second position during a chromatographic separation to provide a thermal gradient during the chromatographic separation is provided. In certain instances, the method may comprise providing a substantially linear thermal gradient during the chromatographic separation by maintaining the heating device at a substantially constant temperature during the chromatographic separation. In other instances, the method may comprise providing a substantially linear thermal gradient during the chromatographic separation using a cooling device thermally coupled to the heating device. In certain configurations, the cooling device can be moved during the chromatographic separation. In other configurations, the cooling device may remain in a stationary position during the chromatographic separation. In some examples, the method comprises moving the heating device from the first position to the second position using a motor coupled to the heating device. In other examples, the method comprises providing power to the motor using a DC power source electrically coupled to the motor. In further examples, the method comprises providing a non-linear thermal gradient using the heating device. In other examples, the method comprises configuring the chromatography system with a processor. In some instances, the method comprises configuring the processor to wirelessly couple to a mobile device that receives chromatography information from the system during the chromatographic separation.

In certain examples, a method comprising providing a heating device configured to thermally couple to a chromatography column at an inlet section of the chromatography column in a first position and to thermally couple to the chromatography column at a section downstream from the inlet section in a second position, the heating device configured to receive the chromatography column during movement of the chromatography column in a longitudinal dimension along the heating device from the first position to the second position during a chromatographic separation to provide a thermal gradient to the chromatography column during the chromatographic separation is described. In some examples, the method comprises providing a substantially linear thermal gradient during the chromatographic separation by maintaining the heating device at a substantially constant temperature during the chromatographic separation. In other examples, the method comprises providing a substantially linear thermal gradient during the chromatographic separation using a cooling device thermally coupled to the heating device. In further instances, the method comprises moving the cooling device during the chromatographic separation. In additional instances, the method comprises maintaining the cooling device in a stationary position during the chromatographic separation. In further instances, the method comprises moving the chromatography column from the first position to the second position using a motor coupled to the chromatography column. In some examples, the method comprises providing power to the motor using a DC power source electrically coupled to the motor. In other examples, the method comprises providing a non-linear thermal gradient using the heating device. In certain embodiments, the method comprises configuring the chromatography system with a processor. In further instances, the method comprises configuring the processor to wirelessly couple to a mobile device that receives chromatography information from the system during the chromatographic separation.

In other examples, a method of performing gas chromatography comprises providing a heating device configured to thermally couple to inner surfaces of a section of a chromatography column in a first position of the heating device and configured to thermally couple to inner surfaces of a different section of the chromatography column in a second position, the heating device configured to move from the first position to the second position to provide a thermal gradient during a gas chromatographic separation. In some instances, the method comprises providing a cooling device configured to thermally couple to the heating device, the heating device and cooling device together configured to provide a substantially linear thermal gradient during the gas chromatographic separation. In further embodiments, the method comprises providing the substantially linear thermal gradient during the chromatographic separation by maintaining one end of the heating device at a substantially constant temperature during the chromatographic separation. In some examples, the method comprises moving the cooling device during the chromatographic separation. In other instances, the method comprises maintaining the cooling device in a stationary position during the chromatographic separation. In some embodiments, the method comprises moving the heating device from the first position to the second position using a motor coupled to the heating device. In additional configurations, the method comprises providing power to the motor using a DC power source electrically coupled to the motor. In some embodiments, the method comprises providing a non-linear thermal gradient using the heating device. In other examples, the method comprises configuring the chromatography system with a processor. In some examples, the method comprises configuring the processor to wirelessly couple to a mobile device that receives chromatography information from the system during the chromatographic separation.

In certain examples, a method of performing gas chromatography comprises providing a heating device configured to thermally couple to inner surfaces of a section of a chromatography column in a first position of the heating device and configured to thermally couple to inner surfaces of a different section of the chromatography column in a second position, the heating device configured to receive the chromatography column during movement of the chromatography column from the first position to the second position to provide a thermal gradient to the chromatography column during a gas chromatographic separation. In some instances, the method comprises providing a cooling device configured to thermally couple to the heating device, the heating device and cooling device together configured to provide a substantially linear thermal gradient during the gas chromatographic separation. In other instances, the method comprises providing the substantially linear thermal gradient during the chromatographic separation by maintaining one end of the heating device at a substantially constant temperature during the chromatographic separation. In some examples, the method comprises moving the cooling device during the chromatographic separation. In other examples, the method comprises maintaining the cooling device in a stationary position during the chromatographic separation. In further embodiments, the method comprises moving the chromatography column from the first position to the second position using a motor coupled to the heating device. In other examples, the method comprises providing power to the motor using a DC power source electrically coupled to the motor. In additional examples, the method comprises providing a non-linear thermal gradient using the heating device. In other configurations, the method comprises configuring the chromatography system with a processor. In further embodiments, the method comprises configuring the processor to wirelessly couple to a mobile device that receives chromatography information from the system during the chromatographic separation.

In certain embodiments, a method of separating two or more analytes using a thermal gradient comprises providing a heating device configured to thermally couple to a chromatography column in a column space of a chromatography system, in which the heating device is configured to thermally couple to the inlet section of the chromatography column in a first position and to thermally couple to a section of the chromatography column downstream of the inlet section in a second position, and providing instructions for moving the heating device in a longitudinal direction of the chromatography column from the first position to the second position to provide a thermal gradient to the chromatography column during a chromatographic separation. In some examples, the method comprises providing a chromatography column configured to receive the heating device in an inner space formed by coiling of the chromatography column. In other examples, the method comprises providing a motor configured to couple to the heating device to control movement of the heating device in the longitudinal direction. In additional examples, the method comprises providing a cooling device configured to thermally couple to a section of the chromatography column other than a section where the heating device is thermally coupled, in which the heating device and cooling device together are configured to provide a substantially linear thermal gradient during chromatographic separation using the chromatography column. In other embodiments, the method comprises configuring the cooling device as a fan.

In certain embodiments, a method of separating two or more analytes using a thermal gradient comprises providing a heating device configured to thermally couple to a chromatography column in a column space of a chromatography system, in which the heating device is configured to thermally couple to the inlet section of the chromatography column in a first position and to thermally couple to a section of the chromatography column downstream of the inlet section in a second position, and providing instructions for moving the chromatography column in a longitudinal direction of the chromatography column from the first position to the second position to provide a thermal gradient to the chromatography column during a chromatographic separation. In certain examples, the method comprises providing a chromatography column configured to receive the heating device in an inner space formed by coiling of the chromatography column. In some embodiments, the method comprises providing a motor configured to couple to the chromatography column to control movement of the chromatography column in the longitudinal direction. In certain embodiments, the method comprises providing a cooling device configured to thermally couple to a section of the chromatography column other than a section where the heating device is thermally coupled, in which the heating device and cooling device together are configured to provide a substantially linear thermal gradient during chromatographic separation using the chromatography column. In other instances, the method comprises configuring the cooling device as a fan.

In certain configurations, a portable chromatography system comprises a housing sized and arranged to permit carrying of the system by a human, the housing comprising an injector, a column space configured to receive a chromatography column that fluidically couples to the injector to provide sample injected into the injector to an inlet section of the chromatography column, a heating device configured to thermally couple to the chromatography column in the column space, in which the heating device is configured to thermally couple to the inlet section of the chromatography column in a first position and to thermally couple to a section of the chromatography column downstream of the inlet section in a second position, in which the heating device is configured to move in a longitudinal direction of the chromatography column from the first position to the second position to provide a thermal gradient during chromatographic separation using the heating device, a detector configured to fluidically couple to the chromatography column at an exit end of the chromatography column to receive analyte from the chromatography column, and a processor electrically coupled to the detector. The system may also comprise a motor within the housing and coupled to the heating device and electrically coupled to the processor. The system can also include a DC power source electrically coupled to the processor and positioned within the housing. In some examples, the DC power source is configured as an electrochemical cell, a fuel cell, a solar cell or a wind turbine configured to provide a direct current. In certain examples, the heating device is configured to thermally couple to a column that is one or more of a capillary column, a capillary column bundle and a wafer column.

In certain examples, a portable chromatography system comprises a housing sized and arranged to permit carrying of the system by a human, the housing comprising an injector, a column space configured to receive a chromatography column that fluidically couples to the injector to provide sample injected into the injector to an inlet section of the chromatography column, a heating device configured to thermally couple to the chromatography column in the column space, in which the heating device is configured to thermally couple to the inlet section of the chromatography column in a first position and to thermally couple to a section of the chromatography column downstream of the inlet section in a second position, in which the heating device is configured to receive the chromatography column during movement of the chromatography column in a longitudinal direction from the first position to the second position to provide a thermal gradient during chromatographic separation using the heating device, a detector configured to fluidically couple to the chromatography column at an exit end of the chromatography column to receive analyte from the chromatography column, and a processor electrically coupled to the detector. In certain instances, the system comprises a motor within the housing and coupled to the chromatography column and electrically coupled to the processor. In other instances, the system comprises a DC power source electrically coupled to the processor and positioned within the housing. In some embodiments, the DC power source is configured as an electrochemical cell, a fuel cell, a solar cell or a wind turbine configured to provide a direct current. In certain examples, the heating device is configured to thermally couple to a column that is one or more of a capillary column, a capillary column bundle and a wafer column.

Example 1

Figure 23:
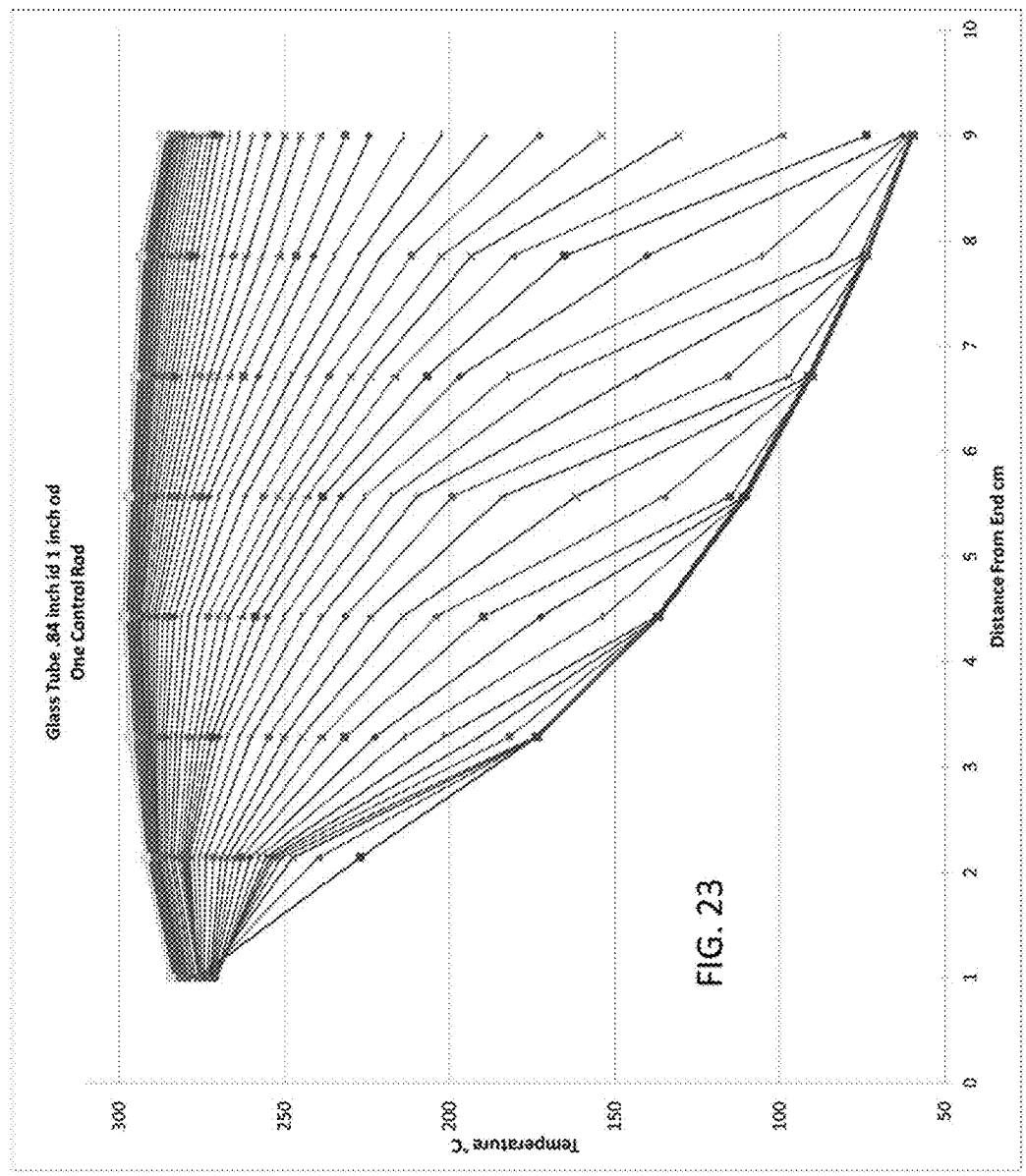
FIG. 23 is a graph showing temperature measurements along a length of a column using a single heating device, in accordance with certain examples.

A system similar to that shown in FIG. 20 (except with only a single heating device) was used to determine the temperature of a column wrapped around a glass tube as the heating device was inserted into the glass tube. The heating device (aluminum rod) was held at a temperature of about 300 deg. C and inserted into the glass tube at a rate of about ¼ inch every 10 seconds. The temperature values as a function of the distance from the end of the glass tube are shown in FIG. 23. Each line represents the temperature profile at a selected time. Insertion of the heating device provided a thermal gradient from one end of the tube to the other.

Example 2

Figure 24:
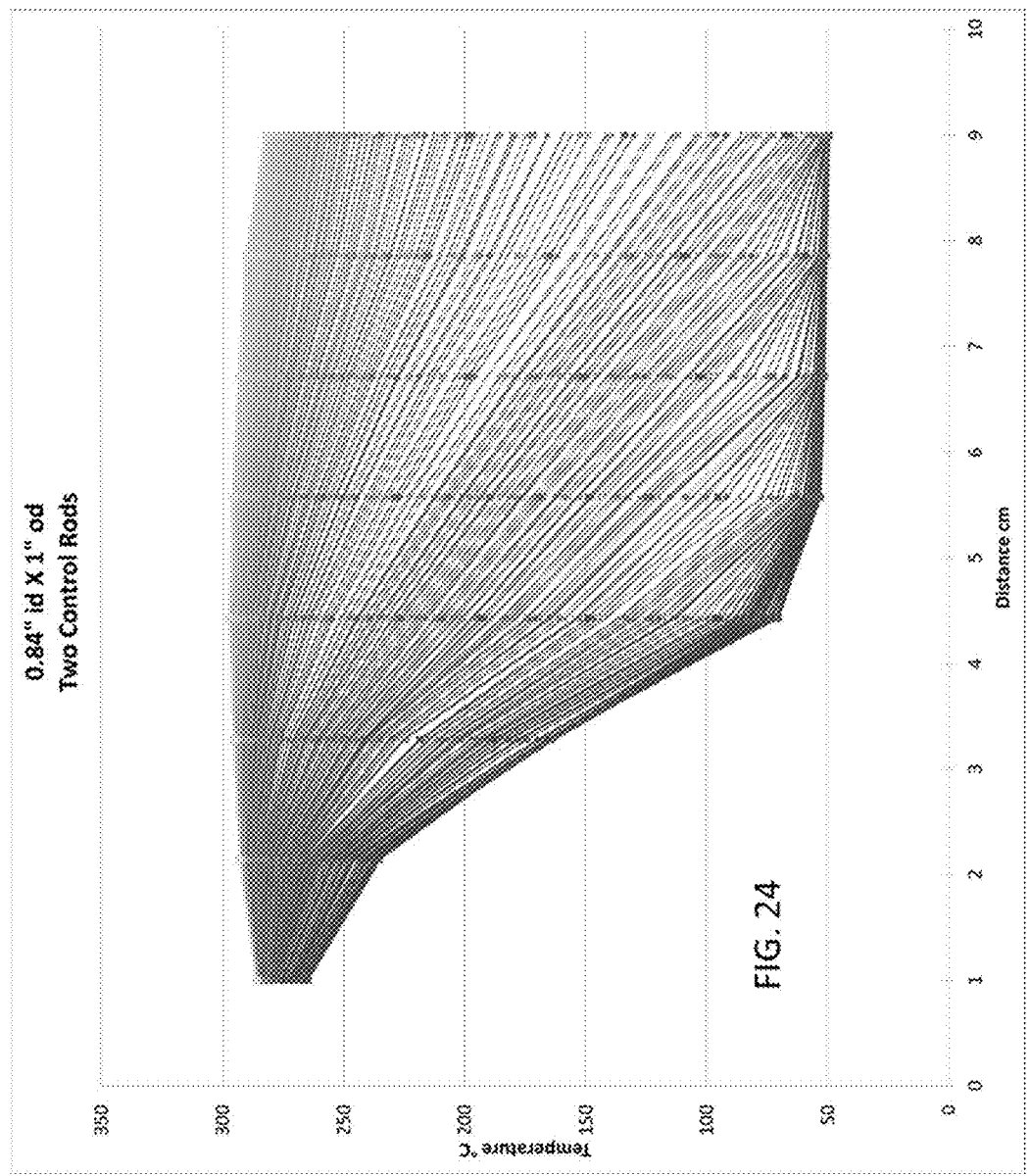
FIG. 24 is a graph showing temperature measurements along a length of a column using two heating devices, in accordance with certain examples.

A system similar to that shown in FIG. 20 was used to determine the temperature of a column wrapped around a glass tube. Two heating devices were used. The cold heating device was held at a temperature of about 50 deg. Celsius. The hot heating device was held at a temperature of about 300 deg. C. Each heating device was configured as an aluminum rod. The heating devices were removed/inserted separately at a rate of about ¼ inch every 10 seconds. The temperature values as a function of the distance from the end of the glass tube are shown in FIG. 24. Each line represents the temperature profile at a selected time. Use of two heating devices provided a steeper gradient and permits for more accurate control of the cool end of the column.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:

1. A gas chromatography system comprising:
  a heating device configured to thermally couple to an inlet section of a gas chromatography column in a first position and to thermally couple to an exit section of the gas chromatography column in a second position, wherein the inlet section of the gas chromatography column is configured to receive a gaseous analyte mixture, wherein the gas chromatography column comprises a separation medium to separate the gaseous analyte mixture using gas chromatography, and wherein separated analytes exit from the gas chromatography column at the exit end of the gas chromatography column, the heating device configured to move longitudinally along the gas chromatography column from the first position to the second position during a gas chromatographic separation wherein the heating device is configured as a cylinder configured to move through an interior space formed by the gas chromatography column; and a processor configured to control movement of the heating device longitudinally along the gas chromatography column from the first position to the second position during the gas chromatographic separation using the heating device to provide a thermal gradient to the gas chromatography column during the gas chromatographic separation.

2. The system of claim 1, further comprising a motor coupled to the heating device and electrically coupled to the processor, the motor configured to move the heating device from the first position to the second position during the gas chromatographic separation.

3. The system of claim 2, further comprising a DC power source electrically coupled to the processor.

4. The system of claim 3, in which the DC power source comprises at least one of an electrochemical cell, a fuel cell, a solar cell or a wind turbine configured to provide a direct current.

5. The system of claim 4, further comprising a display electrically coupled to the processor.

6. The system of claim 4, in which the motor is configured as a stepper motor.

7. The system of claim 4, further comprising a transmitter electrically coupled to the processor.

8. The system of claim 7, in which the transmitter is configured to wirelessly couple to a mobile device.

9. The system of claim 8, in which the transmitter comprises at least one of a Bluetooth device, a near field communication device, a WLAN device, a USB device, a RF device, a cellular device, a radio device, a satellite device, or a GPS device.

10. The system of claim 1, further comprising an oven configured to thermally couple to the gas chromatography column and to receive the heating device and the gas chromatography column.

11. The system of claim 10, in which the oven is configured to operate at a substantially constant temperature during the gas chromatographic separation.

12. The system of claim 1, in which the heating device is the only heating device present in the chromatography system to provide heat to the gas chromatography column.

13. The system of claim 1, further comprising a cooling device thermally coupled to the heating device and the gas chromatography column, the cooling device configured to assist in providing the thermal gradient to the gas chromatography column during the gas chromatographic separation.

14. The system of claim 13, in which the cooling device is configured as one or more of a fan, a Peltier cooler, a cooling rod and a heatsink.

15. The system of claim 13, in which the heating device and the cooling device together are configured to provide a linear thermal gradient along a longitudinal dimension of the gas chromatography column from the inlet section to the exit section during the gas chromatographic separation.

16. The system of claim 1, further comprising a detector configured to fluidically couple to the chromatography column.

17. The system of claim 1, in which the gas chromatograph column comprises a coiled gas chromatography column, and the heating device is configured as a cylinder configured to move through an interior space formed by the coiled gas chromatography column.

18. The system of claim 17, in which the diameter of the cylinder is sized and arranged to receive and contact surfaces of gas chromatography column to provide the thermal gradient to the gas chromatography column.

19. The system of claim 17, in which the heating device is configured to thermally couple to two or more gas chromatography columns during the gas chromatographic separation to provide a temperature gradient to each of the two or more gas chromatography columns.

20. The system of claim 1, further comprising a second heating device configured to thermally couple to the inlet section of the gas chromatography column in a first position and to thermally couple to the exit section of the gas chromatography column in a second position, the second heating device configured to comprise a different temperature than a temperature of the heating device during the gas chromatographic separation.

* * * * *